(12) United States Patent
Srimohanarajah et al.

(10) Patent No.: US 10,993,771 B2
(45) Date of Patent: May 4, 2021

(54) TRACKABLE APPARATUSES AND METHODS

(71) Applicant: SYNAPTIVE MEDICAL INC., Toronto (CA)

(72) Inventors: Kirusha Srimohanarajah, Toronto (CA); Gal Sela, Toronto (CA); Kelly Noel Dyer, Toronto (CA); Dorothy Lui, Toronto (CA); Brent Andrew Bailey, Toronto (CA)

(73) Assignee: SYNAPTIVE MEDICAL INC., Toronto (CA)

( * ) Notice: Subject to any disclaimer, the term of this patent is extended or adjusted under 35 U.S.C. 154(b) by 623 days.

(21) Appl. No.: 15/262,560

(22) Filed: Sep. 12, 2016

(65) Prior Publication Data

US 2018/0071029 A1 Mar. 15, 2018

(51) Int. Cl.
*A61B 34/20* (2016.01)
*A41D 13/11* (2006.01)
(Continued)

(52) U.S. Cl.
CPC .............. *A61B 34/20* (2016.02); *A41D 13/11* (2013.01); *A41D 13/1209* (2013.01); *A61B 34/10* (2016.02); *A61B 34/30* (2016.02); *A61B 46/00* (2016.02); *A61B 46/10* (2016.02); *A61B 90/361* (2016.02); *A61B 90/37* (2016.02); *A61B 90/39* (2016.02); *A61B 2034/2048* (2016.02);
(Continued)

(58) Field of Classification Search
CPC ......... A61B 34/20; A61B 90/39; A61B 90/37; A61B 34/10; A61B 46/10; A61B 90/361; A61B 34/30; A61B 46/00; A61B 2090/364; A61B 2090/363; A61B 2034/2055; A61B 2090/3735; A61B 2090/3937; A61B 2034/2048; A61B 2017/00526; A61B 2034/2051; A41D 13/1209; A41D 13/11
See application file for complete search history.

(56) References Cited

U.S. PATENT DOCUMENTS

| | | | |
|---|---|---|---|
| 6,094,007 A * | 7/2000 | Faul | A61B 90/39 257/E33.056 |
| 7,771,436 B2 * | 8/2010 | Moctezuma De La Barrera | A61B 34/20 606/130 |

(Continued)

FOREIGN PATENT DOCUMENTS

WO WO-2014139019 A1 * 9/2014 ............. G06T 7/337

*Primary Examiner* — Bill Thomson
*Assistant Examiner* — Amy J Shafqat

(57) ABSTRACT

Trackable apparatuses and methods involving at least one arrangement of at least one trackable feature configured for disposition in relation to at least one substrate, each arrangement of the at least one arrangement having a distinct pattern of trackable features configured to facilitate determining at least one of: an identity of at least one object and at least one subject, a disposition of at least one object and at least one subject, a disposition between at least one object and at least one subject, and a disposition among at least one object and at least one subject, and each arrangement of the at least one arrangement configured to optimize tracking by a navigation tracking system, whereby at least one spatial relationship among the at least one object and the at least one subject is optimizable. The navigation tracking system is optionally multi-modal.

12 Claims, 22 Drawing Sheets

(51) Int. Cl.
  *A61B 46/00*   (2016.01)
  *A61B 46/10*   (2016.01)
  *A61B 34/10*   (2016.01)
  *A41D 13/12*   (2006.01)
  *A61B 34/30*   (2016.01)
  *A61B 90/00*   (2016.01)

(52) U.S. Cl.
  CPC ............... *A61B 2034/2051* (2016.02); *A61B 2034/2055* (2016.02); *A61B 2090/363* (2016.02); *A61B 2090/364* (2016.02); *A61B 2090/3735* (2016.02); *A61B 2090/3937* (2016.02); *A61B 2090/3983* (2016.02)

(56) References Cited

U.S. PATENT DOCUMENTS

| | | | | |
|---|---|---|---|---|
| 8,877,541 | B2* | 11/2014 | Argo | H01L 31/035272 438/80 |
| 8,907,245 | B2* | 12/2014 | Cope | G01N 1/04 219/121.6 |
| 9,572,539 | B2* | 2/2017 | Carrat | A61B 5/061 |
| 9,681,798 | B2* | 6/2017 | Hunter | A61B 1/0638 |
| 10,034,713 | B2* | 7/2018 | Yang | A61B 90/39 |
| 10,165,981 | B2* | 1/2019 | Schoepp | A61B 90/361 |
| 10,433,763 | B2* | 10/2019 | Piron | A61B 5/0095 |
| 10,449,005 | B2* | 10/2019 | Christian | A61B 90/39 |
| 10,503,150 | B2* | 12/2019 | Chen | B33Y 50/02 |
| 10,507,063 | B2* | 12/2019 | Zuhars | A61B 34/20 |
| 10,588,699 | B2* | 3/2020 | Richmond | A61B 34/20 |
| 10,786,314 | B2* | 9/2020 | Wood | A61B 6/032 |
| 10,799,316 | B2* | 10/2020 | Sela | A61B 34/10 |
| 2003/0059097 | A1* | 3/2003 | Abovitz | A61B 90/36 382/132 |
| 2007/0039831 | A1* | 2/2007 | Townsend | C25D 11/005 205/324 |
| 2007/0073137 | A1* | 3/2007 | Schoenefeld | A61B 90/36 600/407 |
| 2008/0237341 | A1* | 10/2008 | Fleck | G06K 7/10366 235/385 |
| 2012/0041446 | A1* | 2/2012 | Wong | A61F 2/3859 606/96 |
| 2013/0093866 | A1* | 4/2013 | Ohlhues | G01C 11/04 348/65 |
| 2013/0278631 | A1* | 10/2013 | Border | G02C 5/143 345/633 |
| 2014/0316420 | A1* | 10/2014 | Ballard | A61B 17/7002 606/102 |
| 2016/0113731 | A1* | 4/2016 | Stokes | A61B 34/37 606/130 |
| 2016/0157938 | A1* | 6/2016 | Breisacher | G16H 50/50 703/11 |
| 2016/0265089 | A1* | 9/2016 | Schuh | C22C 9/01 |
| 2016/0324587 | A1* | 11/2016 | Olson | A61B 34/30 |
| 2017/0007353 | A1* | 1/2017 | Fleig | A61B 5/065 |
| 2017/0020627 | A1* | 1/2017 | Tesar | A61B 90/37 |
| 2017/0042622 | A1* | 2/2017 | Yang | A61B 90/30 |
| 2017/0265947 | A1* | 9/2017 | Dyer | A61B 34/20 |
| 2017/0273715 | A1* | 9/2017 | Piron | A61B 34/30 |
| 2017/0281145 | A1* | 10/2017 | Crawford | A61B 17/025 |
| 2017/0304007 | A1* | 10/2017 | Piron | A61B 34/20 |
| 2018/0064496 | A1* | 3/2018 | Hladio | A61B 17/1703 |
| 2018/0116746 | A1* | 5/2018 | Lennertz | A61B 46/10 |
| 2018/0177523 | A1* | 6/2018 | Piron | A61B 17/3421 |
| 2019/0060008 | A1* | 2/2019 | Bailey | A61B 34/20 |
| 2020/0030991 | A1* | 1/2020 | Bailey | B25J 9/1697 |

* cited by examiner

TRACKABLE APPARATUSES AND METHODS

TECHNICAL FIELD

The subject matter of the present disclosure generally relates to feedback and control systems for tracking items, such as patient reference tools, relating to medical procedures, such as image guided medical procedures. More particularly, the subject matter of the present disclosure technically relates to feedback and control systems for tracking items relating to surgical procedures. Even more particularly, the subject matter of the present disclosure technically relates to the feedback and control systems for tracking items relating to image guided surgical procedures.

BACKGROUND

The present disclosure is generally related to image guided medical procedures using a surgical instrument, such as a fibre optic scope, an optical coherence tomography (OCT) probe, a micro ultrasound transducer, an electronic sensor or stimulator, or an access port based surgery.

In the example of a port-based surgery, a surgeon or robotic surgical system may perform a surgical procedure involving tumor resection in which the residual tumor remaining after is minimized, while also minimizing the trauma to the intact white and grey matter of the brain. In such procedures, trauma may occur, for example, due to contact with the access port, stress to the brain matter, unintentional impact with surgical devices, and/or accidental resection of healthy tissue.

Referring to FIG. 1, this diagram illustrates the insertion of an access port into a human brain, for providing access to internal brain tissue during a medical procedure, in accordance with the related art. The access port 12 is inserted into a human brain 10, providing access to internal brain tissue, wherein the access port 12 may include such instruments as catheters, surgical probes, or cylindrical ports, such as the NICO® BrainiPath®. Surgical tools and instruments may then be inserted within the lumen of the access port in order to perform surgical, diagnostic, or therapeutic procedures, such as resection of tumors, as necessary.

Still referring to FIG. 1, access port surgery may be utilized in conjunction with catheters, DBS needles, a biopsy procedure, and also to biopsies and/or catheters in other medical procedures performed on other parts of the body. In the example of a port-based surgery, a straight or linear access port 12 is typically guided down a sulci path of the brain. Surgical instruments would then be inserted down the access port 12. Optical tracking systems may be used with such medical procedures for tracking the position of a part of the instrument that is within line-of-site of the optical tracking camera. These optical tracking systems also require a reference to the patient to know where the instrument is relative to the target (e.g., a tumour) of the medical procedure. However, in the related art, establishing an accurate reference point to the patient has been challenging.

In the field of medicine, imaging and image guidance are a significant component of clinical care. From diagnosis and monitoring of disease, to planning of the surgical approach, to guidance during procedures and follow-up after the procedure is complete, imaging and image guidance provides effective and multifaceted treatment approaches, for a variety of procedures, including surgery and radiation therapy. Targeted stem cell delivery, adaptive chemotherapy regimes, and radiation therapy are only a few examples of procedures utilizing imaging guidance in the medical field.

Advanced imaging modalities such as Magnetic Resonance Imaging ("MRI") have led to improved rates and accuracy of detection, diagnosis and staging in several fields of medicine including neurology, where imaging of diseases such as brain cancer, stroke, Intra-Cerebral Hemorrhage ("ICH"), and neurodegenerative diseases, such as Parkinson's and Alzheimer's, are performed. As an imaging modality, MRI enables three-dimensional visualization of tissue with high contrast in soft tissue without the use of ionizing radiation. This modality is often used in conjunction with other modalities such as Ultrasound ("US"), Positron Emission Tomography ("PET") and Computed X-ray Tomography ("CT"), by examining the same tissue using the different physical principals available with each modality. CT is often used to visualize boney structures and blood vessels when used in conjunction with an intra-venous agent such as an iodinated contrast agent. MRI may also be performed using a similar contrast agent, such as an intravenous gadolinium-based contrast agent having pharmacokinetic properties that enable visualization of tumors and break-down of the blood brain barrier.

In neurosurgery, for example, brain tumors are typically excised through an open craniotomy approach guided by imaging. The data collected in these solutions typically consists of CT scans with an associated contrast agent, such as iodinated contrast agent, as well as MRI scans with an associated contrast agent, such as gadolinium contrast agent. Also, optical imaging is often used in the form of a microscope to differentiate the boundaries of the tumor from healthy tissue, known as the peripheral zone. Tracking of instruments relative to the patient and the associated imaging data is also often achieved by way of external hardware systems such as mechanical arms, or radiofrequency or optical tracking devices. As a set, these devices are commonly referred to as surgical navigation systems.

Three dimensional (3-D) sensor systems are increasingly being used in a wide array of applications, including medical procedures. These sensor systems determine the shape and/or features of an object positioned in a scene of the sensor system's view. In recent years, many methods have been proposed for implementing 3-D modeling systems that are capable of acquiring fast and accurate high resolution 3-D images of objects for various applications.

Triangulation based 3-D sensor systems and methods typically have one or more projectors as a light source for projecting onto a surface and one or more cameras at a defined, typically rectified relative position from the projector for imaging the lighted surface. The camera and the projector therefore have different optical paths, and the distance between them is referred to as the baseline. Through knowledge of the baseline distance as well as projection and imaging angles, known geometric/triangulation equations are utilized to determine distance to the imaged object. The main differences among the various triangulation methods known in the related art lie in the method of projection as well as the type of light projected, typically structured light, and in the process of image decoding to obtain three dimensional data.

A 3-D sensor system may be contemplated as a novel extension of a surgical navigation systems. One popular triangulation based 3-D sensor system is created by Mantis Vision®, which utilizes a single frame structured light active triangulation system to project infrared light patterns onto an environment. To capture 3-D information, a projector overlays an infrared light pattern onto the scanning target.

Thereafter, a digital camera and a depth sensor, synchronized with the projector, capture the scene with the light reflected by the object for at least the timeframe of one frame of the 3-D scan. This technique is applicable even in complete darkness, since the digital camera includes its own illumination; and, in bright environments, the quality of the resulting image depends on the hardware used.

During a related art medical procedure, navigation systems require a registration to transform between the physical position of the patient in the operating room and the volumetric image set, e.g., MRI/CT. Conventionally, this registration is done to the position of a reference tool, which is visible by the tracking system and stays fixed in position and orientation relative to the patient throughout the procedure. This registration is typically accomplished through correspondence touch points, e.g., either fiducial or anatomic points. Such an approach to registration has a number of disadvantages, including requiring fiducials to be placed before scans, requiring points to be identified, providing for a limited number of points, touch point collection is subject to user variability, and the physical stylus used for collecting the points can deform or deflect patient skin position.

Another conventional approach to collecting the touch points in the related art includes performing a surface tracing of the patient drawn as a line which is matched to the image set surface contour using either a stylus pointer or a laser pointer. Such an approach to registration has a number of disadvantages, including providing for a limited number of points, and the physical stylus can deform or deflect patient skin position. Yet another conventional approach to collecting the touch points includes using a mask, which requires a high level of operator training and is operator dependent. This approach also provides only a limited number of points.

Other common limitations of the foregoing conventional approaches to registration include a stylus that needs to remain visible to the tracking system, which may not necessarily be possible depending on a patient's surgical position or may introduce surgical restrictions that need to be accounted in planning, and error accumulation where touch point or tracing collection is of low quality resulting in error propagation through subsequent steps of the registration. Further, using the conventional methods, if registration is lost, re-registration is difficult to be completed again during the surgical procedure.

In the related art, surgery, such as neurosurgery, for example, brain tumors are typically excised through an open craniotomy approach guided by imaging. Optical imaging is often used in the form of a microscope to differentiate the boundaries of the tumor from healthy tissue, known as the peripheral zone. Tracking of instruments relative to the patient and the associated imaging data is also often achieved by way of external hardware systems such as mechanical arms, radiofrequency, or optical tracking devices.

Some related art tracking systems use tracking markers disposed on a surgical instrument for facilitating navigation of such surgical instrument during surgery. Other related art tracking systems involve using tracking markers on a patient that are detectable during scanning or imaging. In such related art tracking systems, prior to treatment, a retroreflective, apertured, disk is applied to the patient precisely at a location defined by a "tattoo" wherein an aperture or hole is at a center of the disk is used to register the disk with the tattoo. The retroreflective, apertured, disk is detectable by a camera. In a related art tracking system, RFID tags are used on or in bandages for verifying or counting various items.

Other related art tracking systems, such as Servo®, do not track the position and gaze of the surgeon during a surgical procedure. As a result, a probability exists that a trajectory of a robotic arm may intersect the position of the surgeon's head. A collision between the surgeon and the robotic arm and/or related instruments is an adverse event experienced in the related art and should be avoided in order to preserve the sterile field. A collision between the surgeon and the robotic arm and/or related instruments may further result in injury to a patient, a surgeon, or other medical personnel who are present. The probability that a collision will occur is increased in medical situations, wherein multiple clinical staff are disposed in, or cross, the optical camera's line of sight.

In yet other related art tracking systems, a tracking sphere is used in conjunction with a tracking camera to merely calculate the distance between tracked tools within the surgical workspace. Surgical drapes are used to ensure that the sterile field is maintained for equipment that cannot be sterilized which must be brought into the field. The equipment is "drop-clothed" so to speak. The tracking sphere is typically unreliable underneath a drape as used in the related art. Also, if the draped equipment requiring tracking, or the part of the draped equipment, is moved during a medical procedure, the tracking camera is unable to continuously track the tracking marker as reliably as when no drape is present.

Accordingly, challenges experienced in the related art include surgical navigation systems that are unduly cumbersome, that provide inaccurate tracking of items, and that are unable to prevent accidental collisions between items and/or personnel in the surgical theatre. Therefore, a need exists for apparatuses and methods that facilitate tracking identifications and locations of objects and subjects in a surgical environment, such as an operating room.

BRIEF SUMMARY

The present disclosure addresses at least many of the foregoing challenges experienced by related art navigation systems and methods, by way of trackable devices and methods, involving retroreflective features, for use with surgical navigation systems, whereby at least one spatial relationship among the at least one object and the at least one subject is optimizable, and whereby accidental collision among items and/or personnel is preventable in an operating room. A key to minimizing trauma is ensuring that the spatial reference of the patient, as well as objects, and other subjects, in an operating room, as detected by the surgical navigation system, is as accurate as possible. In addition, the use of multi-modal imaging or detecting solutions can provide varying degrees of contrast between different tissue types, tissue function, and disease states as well as provide enhanced tracking of all objects and subject in an environment, such as a surgical theatre. Imaging modalities can be used in isolation, or in combination to better differentiate and diagnose disease, as well as in relation to tracking objects and subjects.

In accordance with an embodiment of the present disclosure, a trackable apparatus comprises: at least one arrangement of at least one trackable feature configured for disposition in relation to at least one substrate, each arrangement of the at least one arrangement comprising a distinct pattern of trackable features configured to facilitate determining at least one of: an identity of at least one object and at least one subject, a disposition of at least one object and at least one subject, a disposition between at least one object and at least one subject, and a disposition among at least one object and at least one subject, and each arrangement of the at least one arrangement configured to optimize tracking by a multi-modal tracking system, whereby at least one spatial relationship among the at least one object and the at least one subject is optimizable.

In accordance with an embodiment of the present disclosure, a method of fabricating a trackable apparatus comprises: configuring at least one arrangement of at least one trackable feature for disposition in relation to at least one substrate, configuring at least one arrangement comprising configuring each arrangement of the at least one arrangement in a distinct pattern of trackable features to facilitate determining at least one of: an identity of at least one object and at least one subject, a disposition of at least one object and at least one subject, a disposition between at least one object and at least one subject, and a disposition among at least one object and at least one subject, and configuring at least one arrangement comprising configuring each arrangement of the at least one arrangement to optimize tracking by a multi-modal tracking system, whereby at least one spatial relationship among the at least one object and the at least one subject is optimizable.

In accordance with an embodiment of the present disclosure, a method of optimizing at least one spatial relationship among at least one object and at least one subject by way of a trackable apparatus comprises: providing the trackable apparatus, providing the trackable apparatus comprising: configuring at least one arrangement of at least one trackable feature for disposition in relation to at least one substrate, configuring at least one arrangement comprising configuring each arrangement of the at least one arrangement in a distinct pattern of trackable features to facilitate determining at least one of: an identity of at least one object and at least one subject, a disposition of at least one object and at least one subject, a disposition between at least one object and at least one subject, and a disposition among at least one object and at least one subject, and configuring at least one arrangement comprising configuring each arrangement of the at least one arrangement to optimize tracking by a multi-modal tracking system; and disposing the at least one arrangement of the at least one trackable feature in relation to the at least one substrate.

Some of the features in the present disclosure are broadly outlined in order that the section entitled Detailed Description is better understood and that the present contribution to the art by the present disclosure may be better appreciated. Additional features of the present disclosure are described hereinafter. In this respect, understood is that the present disclosure is not limited in its application to the details of the components or steps set forth herein or as illustrated in the several figures of the drawing, but are capable of being carried out in various ways which are also encompassed by the present disclosure. Also, understood is that the phraseology and terminology employed herein are for illustrative purposes in the description and should not be regarded as limiting.

BRIEF DESCRIPTION OF THE DRAWING

The above, and other, aspects, features, and advantages of several embodiments of the present disclosure will be more apparent from the following Detailed Description as presented in conjunction with the following several figures of the Drawing.

Figure 1:
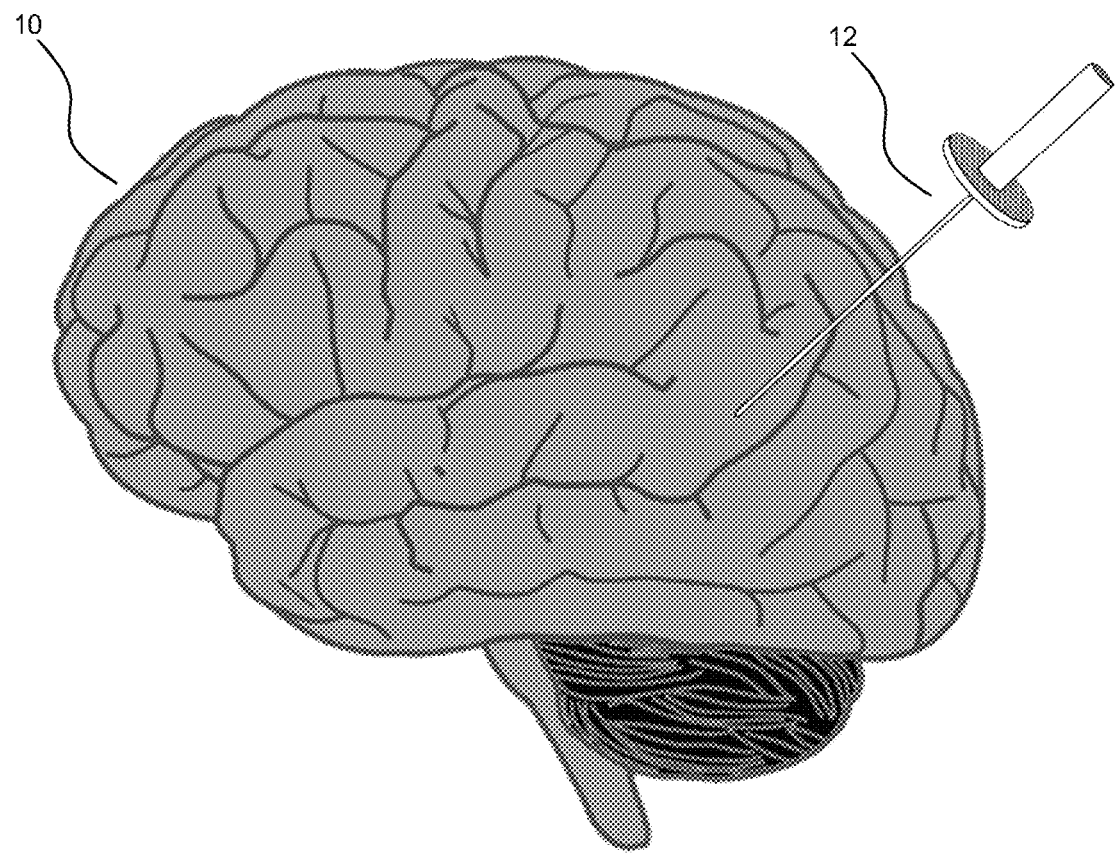
FIG. 1 is a diagram illustrating a perspective view of an access port inserted into a human brain for providing access to internal brain tissue, in accordance with the related art.

Corresponding reference numerals or characters indicate corresponding components throughout the several figures of the Drawing. Elements in the several figures are illustrated for simplicity and clarity and have not necessarily been drawn to scale. For example, the dimensions of some of the elements in the figures may be emphasized relative to other elements for facilitating understanding of the various presently disclosed embodiments. Also, common, but well-understood, elements that are useful or necessary in commercially feasible embodiment are often not depicted in order to facilitate a less obstructed view of these various embodiments of the present disclosure.

DETAILED DESCRIPTION

The systems and methods described herein are useful in the field neurosurgery, including oncological care, neurodegenerative disease, stroke, brain trauma, and orthopedic surgery. However, the subject matter of the present disclosure may extend or apply to other conditions or fields of medicine; and such extensions or applications are encompassed by the present disclosure. The systems and methods described herein encompass surgical processes that are applicable to surgical procedures for brain, spine, knee, and any other region of the body that will benefit from the use of an access port or small orifice to access the interior of an animal body, such as a human body.

Various systems, apparatuses, devices, or processes are below-described and provide examples of the navigation systems and methods embodiments, in accordance with embodiments of the present disclosure. None of the below-described embodiments limits any claimed embodiment; and any claimed embodiment may also encompass systems, apparatuses, devices, or processes which may differ from below-described examples. The claimed embodiments are not limited to systems, apparatuses, devices, or processes having all of the features of any one of the below-described systems, apparatuses, devices, or processes or to features common to some or all of the below-described systems, apparatuses, devices, or processes.

Furthermore, this Detailed Description sets forth numerous specific details in order to provide a thorough understanding of the various embodiments described throughout the present disclosure. However, it will be understood by those of ordinary skill in the art that the embodiments described herein may be practiced without these specific details. In other instances, well-known methods, procedures and components have not been described in detail so as not to obscure the embodiments described herein.

Figure 2:
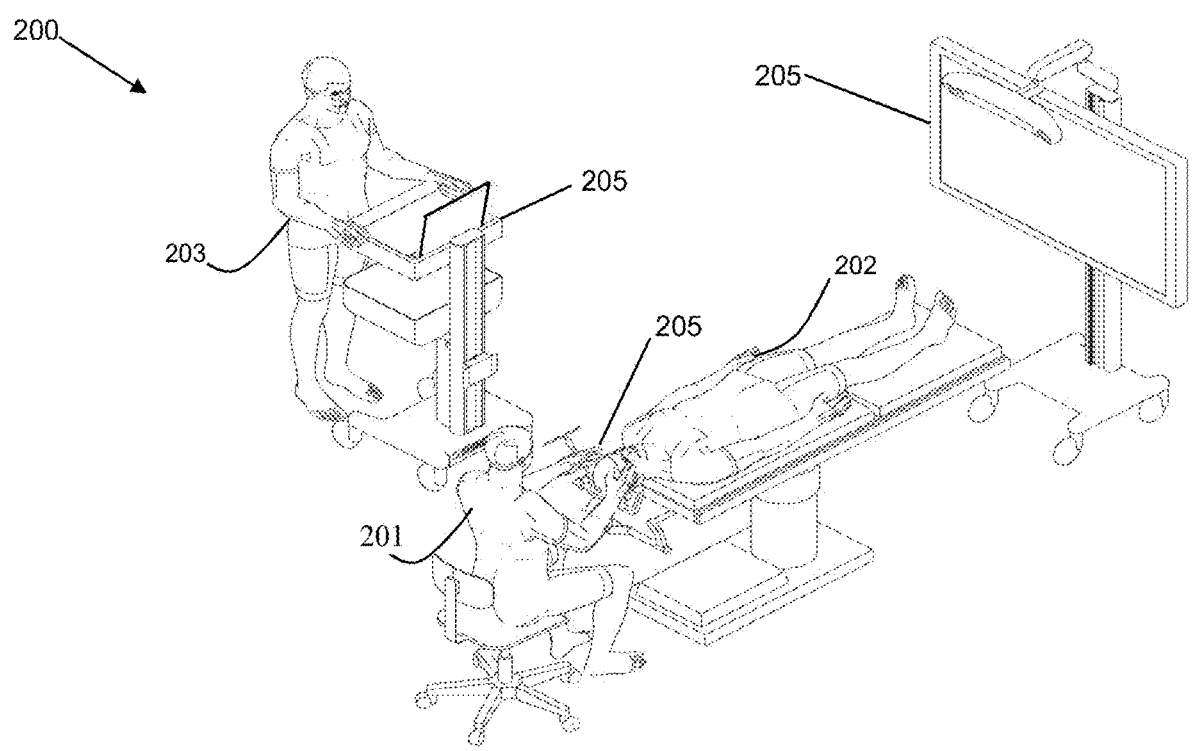
FIG. 2 is a diagram illustrating a perspective view of a navigation system for use in performing a medical procedure, such as a minimally invasive access port-based surgery, in accordance with an embodiment of the present disclosure.

Referring to FIG. 2, this diagram illustrates, in a perspective view, a navigation system 200 for use in performing a medical procedure, such as a minimally invasive access port-based surgery, e.g., navigated image-guided surgery, in accordance with an embodiment of the present disclosure. By example only, a surgeon 201 conducts a surgery on a patient 202 in an operating room OR environment. A medical navigation system 200 comprises: an equipment tower 200a, a tracking system for tracking at least one object, such as at least one of a surgical tool, a surgical device, medical equipment, and the like, and at least one subject, such at least one of: at least one patient, e.g., involving a live tissue donor (some organ transplants, kidneys or lungs) or bone marrow transplants (cancer patients), and at least one medical personnel, e.g., surgeons, anesthesiologists, pathologists, nurses, and the like, in the OR, at least one display device 205, the tracking system facilitating performing a medical procedure. A medical navigation system 200 is further configured for interaction with an operator 203 for facilitating operation, control, and assistance in relation to the tracking system and/or the at least one display device 205.

Figure 3:
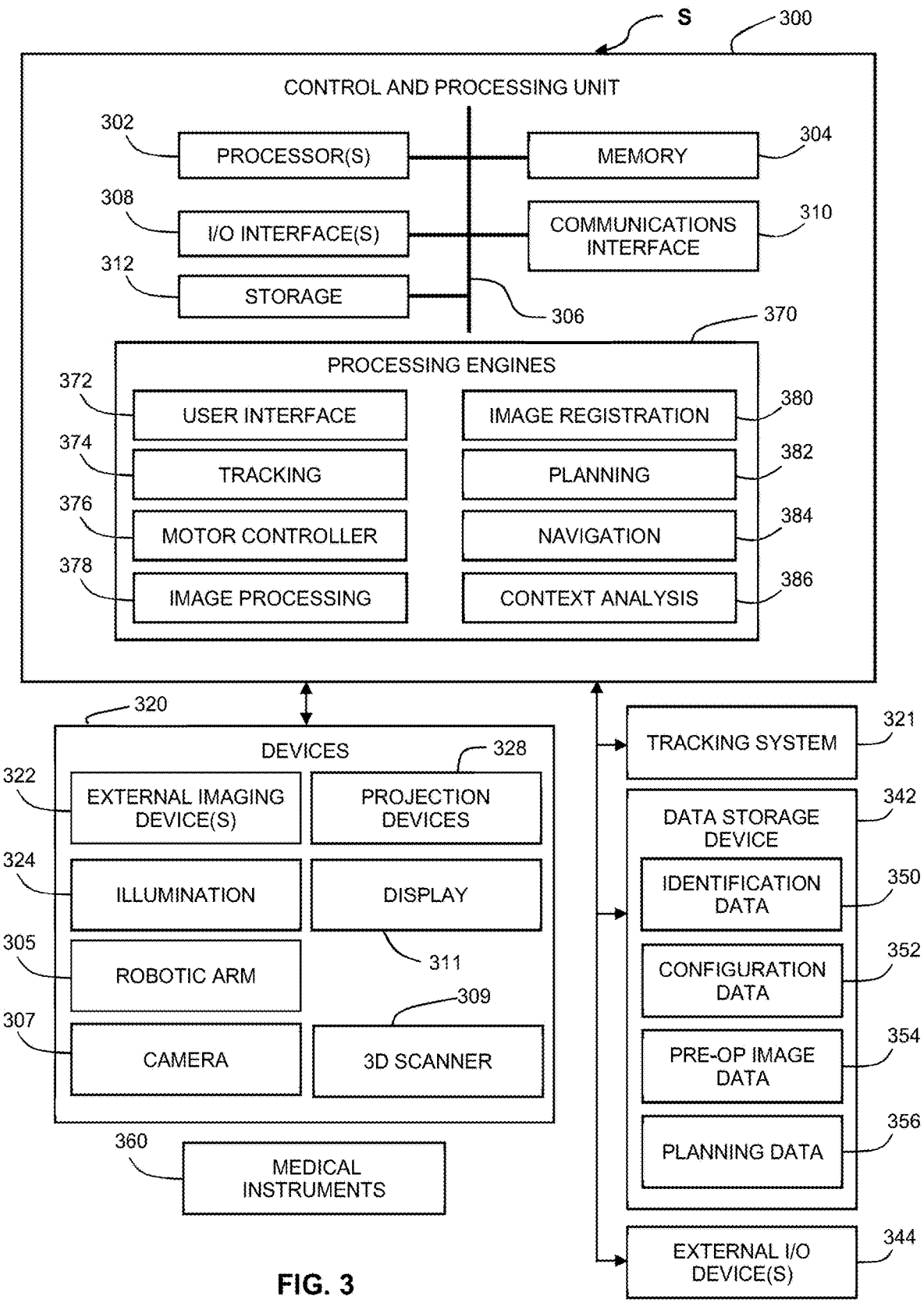
FIG. 3 is a block diagram illustrating a control and processing system or unit for use in the navigation system, as shown in FIG. 2, for performing a medical procedure, in accordance with an embodiment of the present disclosure.

Referring to FIG. 3, this block diagram illustrates a control and processing system or unit 300 for use in the navigation system 200, as shown in FIG. 2, for performing a medical procedure, in accordance with an embodiment of the present disclosure. By example only, the control and processing system 300 comprises at least one processor 302, a memory 304, a system bus 306, at least one input/output (I/O) interface 308, a communication interface 310, and a storage device 312. The control and processing system 300 is interfaceable with other external devices, such as a tracking system 321, data storage 342, and external user input and output devices 344, which may comprise, for example, at least one of a display, a keyboard, a mouse, sensors attached to medical equipment, a foot pedal, a microphone, and a speaker.

Still referring to FIG. 3, data storage 342 comprises any suitable data storage device, such as a local or remote computing device, e.g., a computer, a hard drive, a digital media device, and a server, the data storage device configured to store a database. For example, the data storage device 342 is configured to store identification data 350 for identifying at least one medical instrument 360 and configuration data 352 that associates customized configuration parameters with at least one medical instrument 360. Data storage device 342 may also include preoperative image data 354 and/or medical procedure planning data 356. Although data storage device 342 comprises a single device by example only; however, understood is that, in other embodiments, data storage device 342 comprises a plurality of storage devices 342.

Still referring to FIG. 3, medical instruments 360 are identifiable by the control and processing unit 300. Medical instruments 360 are capable of coupling with and are controllable by the control and processing unit 300. Alternatively, the medical instruments 360 are operable, or otherwise employed, independent of the control and processing unit 300. The tracking system 321 tracks at least one medical instrument 360 and spatially registers the at least one medical instrument 360 in relation to an intra-operative reference frame. For example, the medical instruments 360 comprise tracking spheres recognizable by a tracking camera 307. In one example, the tracking camera 307 comprises an infrared (IR) tracking camera. In another example, as sheath placed over a medical instrument 360 is couple-able with, and controlled by, the control and processing unit 300. The control and processing unit 300 is also interfaceable with a number of configurable devices, and may intra-operatively reconfigure at least one such device based on configuration parameters obtained from the configuration data 352. Examples of the devices 320, include at least one external imaging device 322, at least one illumination device 324, a robotic arm 305, at least one projection device 328, a display 211, and a 3-D scanner 309.

Still referring to FIG. 3, the control and processing unit 300 can be implemented via processor(s) 302 and/or memory 304. For example, the functionalities described herein can be partially implemented via hardware logic in the processor 302 and partially using the instructions stored in memory 304, at least one processing module, or an engine 370. Example processing modules include, but are not limited to, a user interface engine 372, a tracking module 374, a motor controller 376, an image processing engine 378, an image registration engine 380, a procedure planning engine 382, a navigation engine 384, and a context analysis module 386. While the example processing modules are shown separately, the processing modules 370 may be stored in the memory 304; and the processing modules 370 may be collectively referred to as processing modules 370.

Still referring to FIG. 3, that the system 300 is not limited to the components as shown herein. The control and processing system 300 may comprise an external component or device. In one example, a navigation module 384 comprises an external navigation system integrable with the control and processing system 300. Some embodiments of the system 300 are implementable by using a processor 302 without using additional instructions stored in the memory 304. Some embodiments of the system 300 are implementable by using the instructions stored in the memory 304 for execution by at least one general purpose microprocessors. Thus, the present disclosure is not limited to a specific configuration of hardware and/or software, but encompasses any configuration of hardware, firmware, and/or software.

Still referring to FIG. 3, while some embodiments of the present disclosure are implementable in fully functioning computers and computer systems, various embodiments are capable of being distributed as a computing product in a variety of forms and are capable of being applied regardless of the particular type of machine or computer readable media used to actually effect the distribution. At least some aspects disclosed can be embodied, at least in part, in software. That is, the techniques may be carried out in a computer system or other data processing system in response to its processor, such as a microprocessor, executing sequences of instructions contained in a memory, such as ROM, volatile RAM, non-volatile memory, cache or a remote storage device.

Still referring to FIG. 3, in some embodiments, a computer readable storage medium is used to store software and data which, when executed by a data processing system, causes the system to perform various methods. The executable software and data may be stored in various places including for example ROM, volatile RAM, nonvolatile memory and/or cache. Portions of this software and/or data may be stored in any one of these storage devices. Examples of computer-readable storage media include, but are not limited to, recordable and non-recordable type media such as volatile and non-volatile memory devices, read only memory (ROM), random access memory (RAM), flash memory devices, floppy and other removable disks, magnetic disk storage media, optical storage media (e.g., compact discs (CDs), digital versatile disks (DVDs), etc.), among others. The instructions may be embodied in digital and analog communication links for electrical, optical, acoustical or other forms of propagated signals, such as carrier waves, infrared signals, digital signals, and the like.

The storage medium may be the internet cloud, or a computer readable storage medium such as a disc.

Still referring to FIG. 3, at least some of the methods described herein are capable of being distributed in a computer program product comprising a computer readable medium that bears computer usable instructions for execution by one or more processors, to perform aspects of the methods described. The medium may be provided in various forms such as, but not limited to, one or more diskettes, compact disks, tapes, chips, USB keys, external hard drives, wire-line transmissions, satellite transmissions, internet transmissions or downloads, magnetic and electronic storage media, digital and analog signals, and the like. The computer useable instructions may also be in various forms, including compiled and non-compiled code.

Still referring to FIG. 3, according to one aspect of the present disclosure, the navigation system 200, comprising the control and processing unit 300, provides tools to the neurosurgeon that will lead to the most informed, least damaging neurosurgical operations. In addition to removal of brain tumours and intracranial hemorrhages (ICH), the navigation system 200 can also be applied to a brain biopsy, a functional/deep-brain stimulation, a catheter/shunt placement procedure, open craniotomies, endonasal/skull-based/ENT, spine procedures, and other parts of the body such as breast biopsies, liver biopsies, etc. While several examples have been provided, aspects of the present disclosure may be applied to any suitable medical procedure.

Figure 4A:
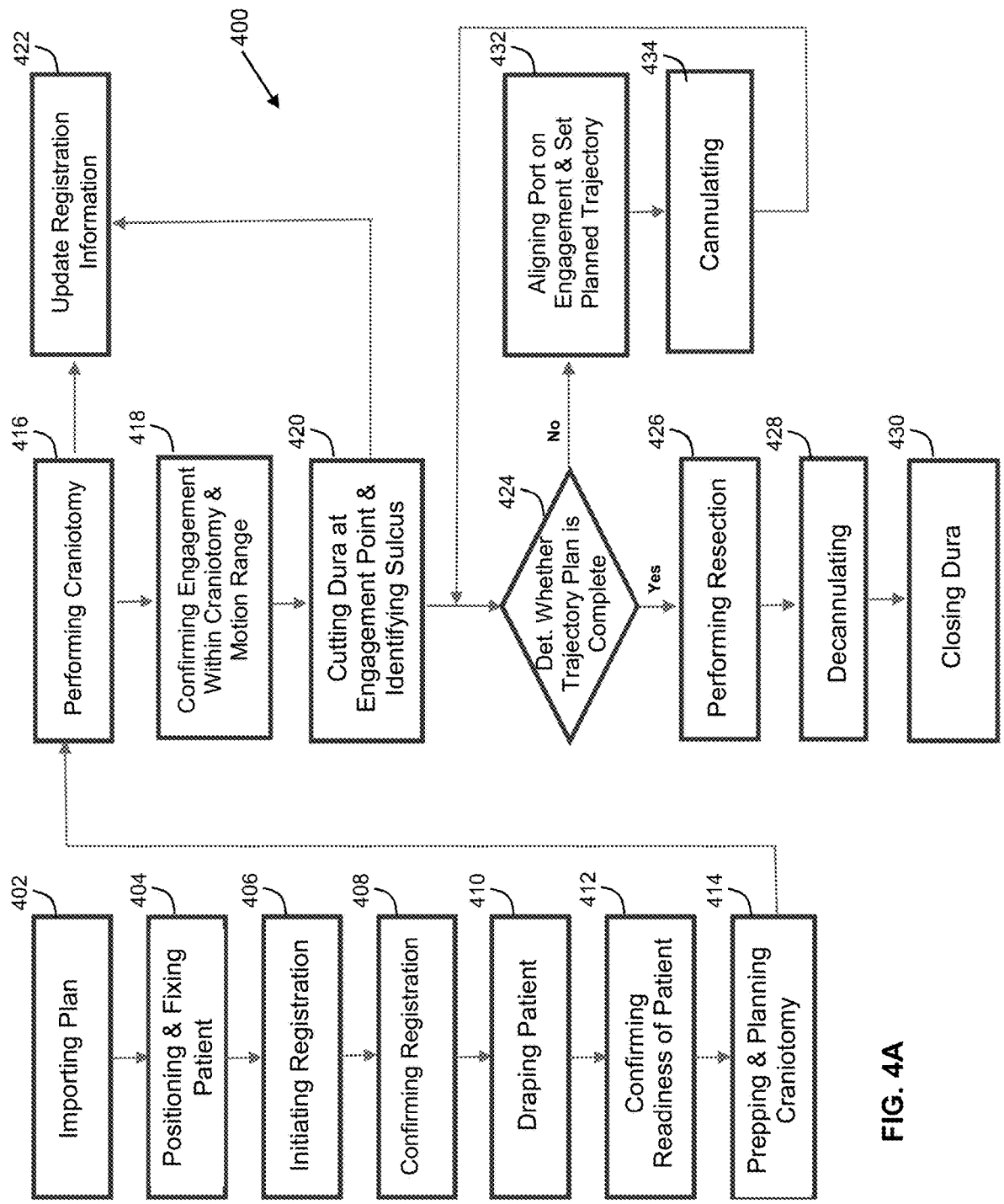
FIG. 4A is a flow chart illustrating a method of using the navigation system, as shown in FIG. 2, comprising the control and processing system, as shown in FIG. 3, for performing a medical procedure, in accordance with an embodiment of the present disclosure.

Referring to FIG. 4A, this flow chart illustrates a method 400 of using the navigation system 200, as shown in FIG. 2, comprising the control and processing system 300, as shown in FIG. 3, for performing a medical procedure, in accordance with an embodiment of the present disclosure. The medical procedure may comprise a port-based surgical procedure. The method 400 comprises: importing a port-based surgical plan, as indicated by block. A detailed description of the process to create and select a surgical plan is outlined in international publication WO/2014/139024, entitled "PLANNING, NAVIGATION AND SIMULATION SYSTEMS AND METHODS FOR MINIMALLY INVASIVE THERAPY," claiming priority to U.S. Provisional Patent Application Ser. Nos. 61/800,155 and 61/924,993, all of which are hereby incorporated by reference in their entirety.

Still referring to FIG. 4A, once the plan has been imported into the navigation system 200, as indicated by block 402, the method 400 further comprises positioning and affixing the patient is affixed into position by using a body holding mechanism, as indicated by block 404, wherein positioning and affixing comprises confirming that the head position is consistent with the patient plan in the navigation system 200. For example, a computer or controller, forming part of the equipment tower 200a of medical navigation system 200, is configurable to implement confirming that the head position is consistent with the patient plan in the navigation system 200.

Still referring to FIG. 4A, the method 400 further comprises initiating registration of the patient, as indicated by block 406. The phrase "registration" or "image registration" refers to the process of transforming different sets of data into one coordinate system. Data may includes multiple photographs, data from different sensors, times, depths, or viewpoints. The process of "registration" is used in the present application for medical imaging in which images from different imaging modalities are co-registered. Registration is used in order to be able to compare or integrate the data obtained from these different modalities.

Still referring to FIG. 4A, initiating registration of the patient, as indicated by block 406, of the method 400 encompasses at least one of numerous registration techniques. Non-limiting examples include intensity-based methods that compare intensity patterns in images via correlation metrics, while feature-based methods find correspondence between image features such as points, lines, and contours. Image registration methods may also be classified according to the transformation models they use to relate the target image space to the reference image space. Another classification can be made between single-modality and multi-modality methods. Single-modality methods typically register images in the same modality acquired by the same scanner or sensor type, for example, a series of magnetic resonance (MR) images may be co-registered, while multi-modality registration methods are used to register images acquired by different scanner or sensor types, for example in magnetic resonance imaging (MRI) and positron emission tomography (PET). In the present disclosure, multi-modality registration methods may be used in medical imaging of the head and/or brain as images of a subject are frequently obtained from different scanners. Examples include registration of brain computerized tomography (CT)/MRI images or PET/CT images for tumor localization, registration of contrast-enhanced CT images against non-contrast-enhanced CT images, and registration of ultrasound and CT.

Still referring to FIG. 4A, the method 400 further comprises: confirming registration, as indicated by block 408; draping the patient, as indicated by block 410; confirming readiness of the patient, as indicated by block 412; preparing and planning a craniotomy, as indicated by block 414; cutting a cranium, thereby performing the craniotomy, as indicated by block 416, and updating registration information, as indicated by block 422; confirming engagement within a space defined by the craniotomy and a range of motion, as indicated by block 418; cutting dura at an engagement point and identifying sulcus, as indicated by block 420, and updating registration information, as indicated by block 422; determining whether a trajectory plan is complete, as indicated by block 424, and, if so, performing a resection, as indicated by block 436, decannulating, as indicated by block 428, and closing dura, as indicated by block 430; and, if not, aligning the port on an engagement point and setting the port, as indicated by block 432, cannulating, as indicated by block 434, and determining whether a trajectory plan is complete, as indicated by block 424.

Figure 4B:
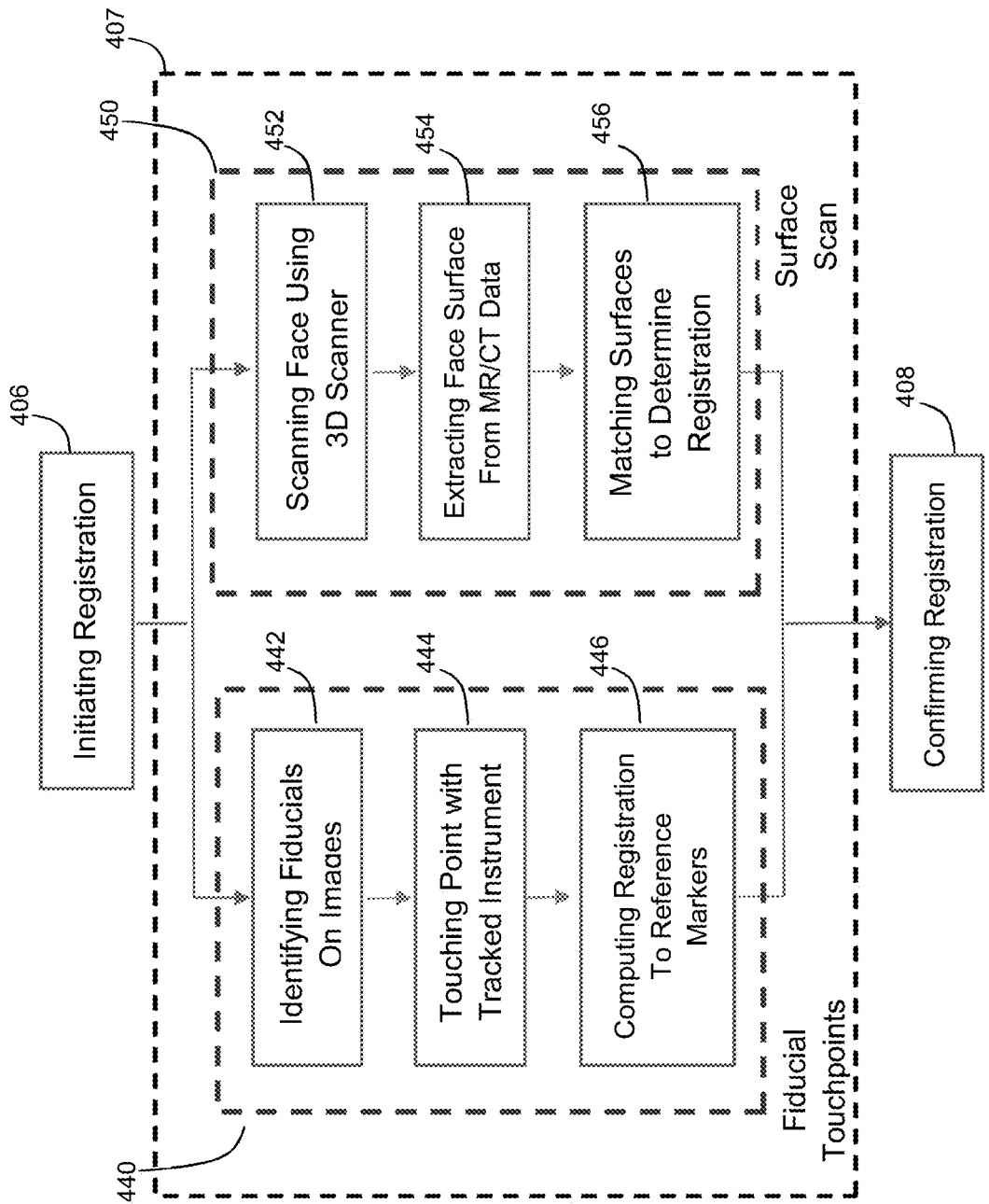
FIG. 4B is a flow chart illustrating a method of registering a patient, such as after initiating registration and before confirming registration, as shown in FIG. 4A, for performing a medical procedure by way of the navigation system, in accordance with an embodiment of the present disclosure.

Referring to FIG. 4B, this flow chart illustrates a method 407 of registering a patient, such as after initiating registration, as indicated by 406, of the method 400, and before confirming registration, as indicated by block 408, of the method 400, as shown in FIG. 4A, for performing a medical procedure by way of the navigation system 200, in accordance with an embodiment of the present disclosure. The method 400 further comprises the method 407, in accordance with an embodiment of the present disclosure. If the use of fiducial touch points is contemplated, the method 407 involves performing fiducial steps, as indicated by block 440, comprising: identifying fiducials, fiducial markers, or reference markers on images, as indicated by block 442, touching the touch points with a tracked instrument, as indicated by block 444; and computing the registration to reference markers by way of the navigation system, as indicated by block 446.

Still referring to FIG. 4B, if the use of fiducial touch points is not contemplated, e.g., if a surface scan is alternatively contemplated, the method 407 involves performing surface scan steps, as indicated by block 450, comprising: scanning a face by way of a 3-D scanner, thereby providing in situ scanned face data, as indicated by block 452; extracting the face surface from MR/CT data scanner, as indicated by block 454; and matching the in situ scanned face data with the extracted face data to determine whether registration is sufficient by way of a plurality of data points, as indicated by block 456. Upon completion of either the method 440 or the method 450, the method 400 comprises confirming registration by using the data extracted for computation, as indicated by block 408, as shown in FIG. 4A.

Referring back to FIG. 4A, after confirming registration by using the data extracted for computation, as indicated by block 408, the method 400 comprises draping the patient, as indicated by block 410. Typically, draping involves covering the patient and surrounding areas with a sterile barrier to create and maintain a sterile field during the surgical procedure. The purpose of draping is to eliminate the passage of microorganisms, e.g., bacteria, viruses, or prions, between non-sterile and sterile areas. At this point, related art navigation systems require that the non-sterile patient reference is replaced with a sterile patient reference of identical geometry location and orientation. Numerous mechanical methods may be used to minimize the displacement of the new sterile patient reference relative to the non-sterile one that was used for registration, but some error is inevitable in the related art. This error directly translates into registration error between the surgical field and pre-surgical images. In fact, the further away points of interest are from the patient reference, the worse the error will be. In the present disclosure, however, the navigation system 200 is used in conjunction with a trackable apparatus for eliminating such related art errors (FIGS. 14-19).

Still referring back to FIG. 4A, upon completion of draping (block 410), the patient engagement points are confirmed (block 412) and then the craniotomy is prepared and planned (block 414). Upon completion of the preparation and planning of the craniotomy (block 414), the craniotomy is cut and a bone flap is temporarily removed from the skull to access the brain (block 416). Registration data is updated with the navigation system at this point (block 422). The engagement within craniotomy and the motion range are confirmed (block 418). The procedure advances to cutting the dura at the engagement points and identifying the sulcus (block 420). The cannulation process is initiated (block 424). Cannulation involves inserting a port into the brain, typically along a sulci path as identified at block 420, along a trajectory plan. Cannulation is typically an iterative process that involves repeating the steps of aligning the port on engagement and setting the planned trajectory (block 432) and then cannulating to the target depth (block 434) until the complete trajectory plan is executed (block 424).

Still referring back to FIG. 4A, once cannulation is complete, the surgeon then performs resection (block 426) to remove part of the brain and/or tumor of interest. The surgeon then decannulates (block 428) by removing the port and any tracking instruments from the brain. Finally, the surgeon closes the dura and completes the craniotomy (block 430). Some aspects of the method 400 are specific to port-based surgery, such portions of the steps indicated by blocks 428, 420, and 434, but the appropriate portions of the steps indicated by blocks 428, 420, and 434 are optionally performed or suitably modified when performing non-port based surgery.

Still referring back to FIG. 4A, when performing a surgical procedure using the navigation system 200, as shown in FIGS. 4A and 4B, the navigation system 200 acquires and maintains a reference of the location of the tools in use as well as the patient in three dimensional (3-D) space. In other words, during a navigated neurosurgery, a tracked reference frame is used that is fixed relative to the patient's skull. During the registration phase of a navigated neurosurgery, e.g., as indicated by block 406, as shown in FIGS. 4A and 4B, a transformation is calculated that maps the frame of reference of preoperative MM or CT imagery to the physical space of the surgery, specifically the patient's head. This mapping may be accomplished by the navigation system 200 tracking locations of fiducial markers fixed to the patient's head, relative to the static patient reference frame. The patient reference frame is typically rigidly attached to the head fixation device, such as a Mayfield clamp. Registration is typically performed before the sterile field has been established, e.g., by performing the step indicated by block 410.

Still referring back to FIG. 4A, the method 400 overcomes many related art problems. For instance, most related art navigation systems require the patient reference be exchanged during the draping phase and the original patient reference frame used for registration is replaced with a sterile patient reference frame. This related art exchange can cause a loss of accuracy. Other related art systems may require the non-sterile reference frame to be draped with a sterile, transparent plastic surgical drape. Where tracking spheres are used in conjunction with an infrared (IR) tracking camera, visibility through this drape can cause optical distortion of the measured reference position and can cause loss of accuracy. This process is also operator and set-up dependent, being affected by how the sterile drape is positioned and how tightly it is formed around the reference frame.

Still referring back to FIG. 4A, the method 400 overcomes many other related art problems. For instance, throughout a navigated surgery, the patient reference frame is sometimes bumped by the surgeon or others involved into the procedure. A bump that is strong enough could cause a shift in the frame's location and therefore create a misregistration. In order to address the shortcomings of conventional systems outlined above, according to one aspect of the present disclosure, a patient reference design is provided that incorporates a removable sterile cover. According to another aspect of the present description, a sensor may be attached to, or embedded in, the patient reference frame to provide the medical navigation system 200 with information that can be used to determine whether the patient reference frame is bumped with enough force such that the frame's location requires re-registration.

Still referring back to FIG. 4A, the draping step of the method 400 comprises using a sterile drape having a plastic lens that is placed over the patient face, the plastic lens containing the tracking markers. In one example, the sterile cover maybe a substantially rigid lens. In one example, the markers could be active IR markers or passive reflective spheres. The sterile cover may not cause significant distortion like a standard drape would. The sterile cover may have a transparent plastic sock that extends downward from the cover to cover the rest of the patient reference and patient reference mounting arm and extension. The patient reference may be designed to permit +/−45 degree line-of-sight between the tracking camera 307 (e.g., a Northern Digital Polaris Spectra) and the patient reference. The navigation system 200 further comprises force sensors and/or accelerometers, either wired or wirelessly; and the navigation system 200 may display a warning and/or force re-registration if too great of a force and/or acceleration is imparted on the patient reference.

Figure 5:
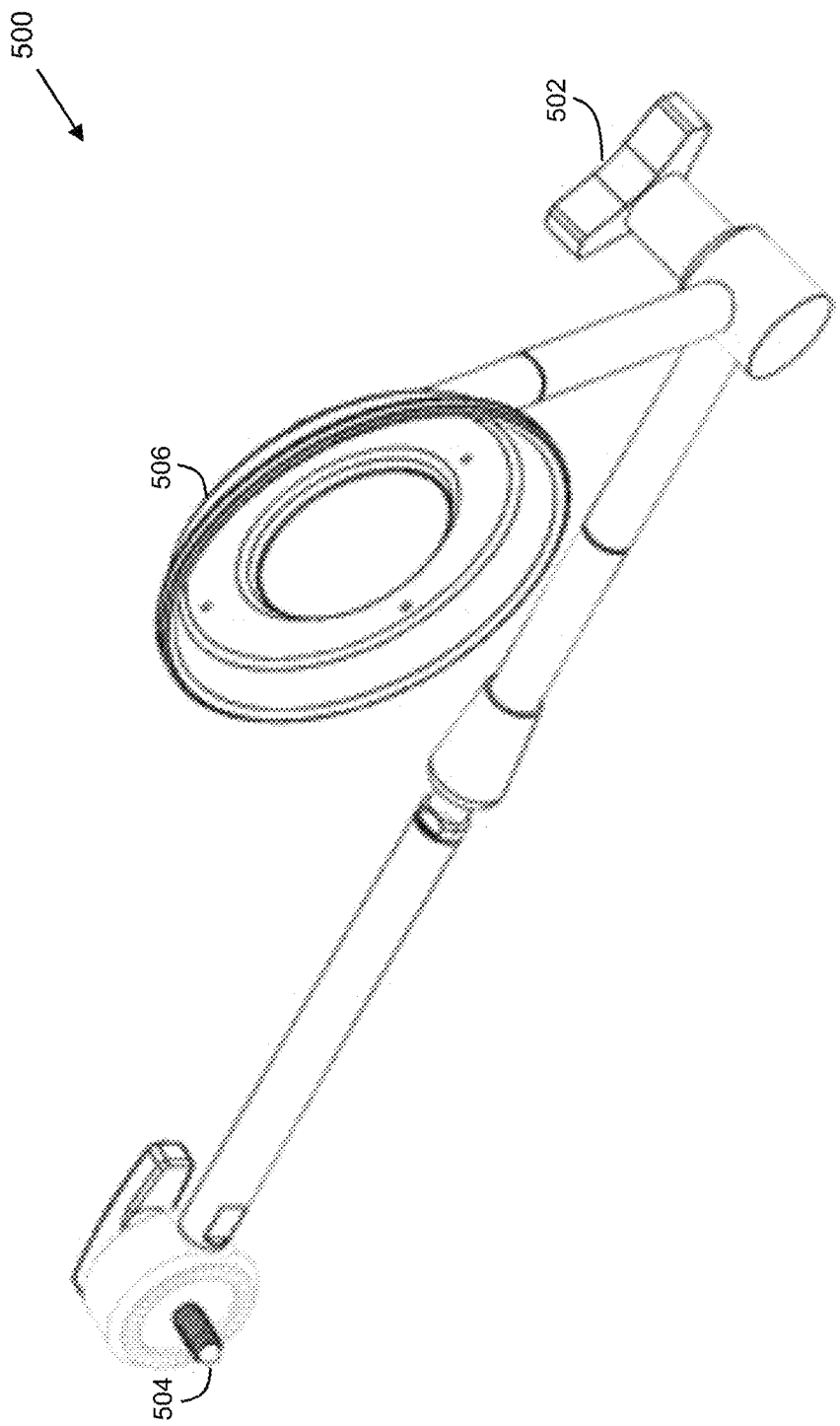
FIG. 5 is a diagram illustrating a perspective view of an arm, such as a robotic arm, for at least one of holding, retaining, and maneuvering a patient reference device for performing a medical procedure by way of the navigation system, in accordance with an embodiment of the present disclosure.

Referring to FIG. 5, this diagram illustrates, in a perspective view, an arm 500, such as a robotic arm 305, for at least one of holding, retaining, and maneuvering a patient reference device 506 for performing a medical procedure by way of the navigation system 200, in accordance with an embodiment of the present disclosure. The arm 500 may also be referred to as a patient reference arm 500, the patient reference arm 500 comprising a fastener, such as a tightening screw 502, for securing the patient reference arm 500 once patient reference arm 500 has been suitably adjusted. The patient reference arm 500 may attach to a Mayfield head holder or other suitable head holding device using a mounting bolt 504. In another example, the patient reference arm 500 attaches directly to a patient bed, wherein the spatial relationship between the receiving device for the mounting bolt 504 and the patient's head is static and known by navigation system 200. The mounting bolt 504 may secure the patient reference arm 500 to a Mayfield clamp. Once the tightening screw 502 is tightened, the arm 500 may not pivot; the user may clock the arm 500 to his desired position using a starburst connection. Once the screw 502 is tightened, a rigid connection between the Mayfield clamp and the arm 500 is provided. While one example of an arm 500 for connecting a patient reference device 506 with a head holding device has been shown, any suitable arm or connecting mechanism may be used according to a particular application and is also encompassed by the present disclosure.

Figure 6B:
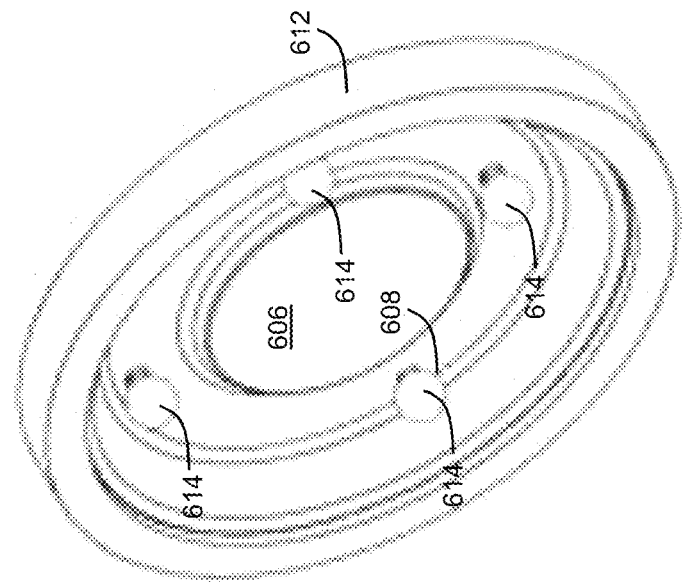
FIG. 6B is a diagram illustrating a perspective view of the patient reference device, as shown in FIG. 6A, comprising a cover and a housing, for performing a medical procedure by way of the navigation system, in accordance with an embodiment of the present disclosure.
Figure 6A:
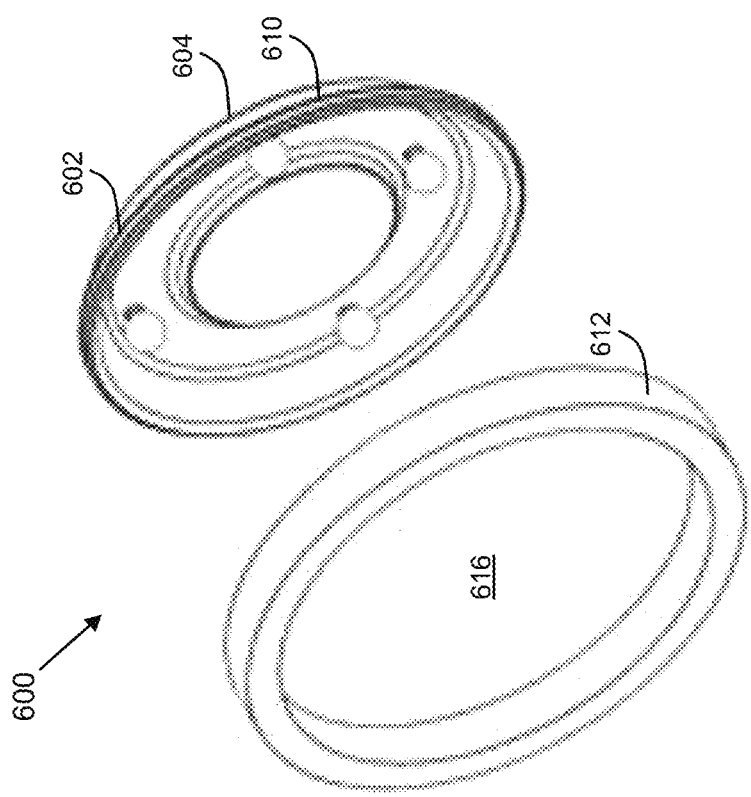
FIG. 6A is a diagram illustrating an exploded perspective view of a patient reference device, comprising a cover and a housing, for performing a medical procedure by way of the navigation system, in accordance with an embodiment of the present disclosure.

Referring to FIG. 6A, this diagram illustrates, in an exploded perspective view, a patient reference device 600, comprising a cover 612 and a housing 602, for performing a medical procedure by way of the navigation system 200, in accordance with an embodiment of the present disclosure.

Referring to FIG. 6B, this diagram illustrates, in a perspective view, the patient reference device 600, as shown in FIG. 6A, comprising a cover 612 and a housing 602, for performing a medical procedure by way of the navigation system 200, in accordance with an embodiment of the present disclosure.

Figure 7:
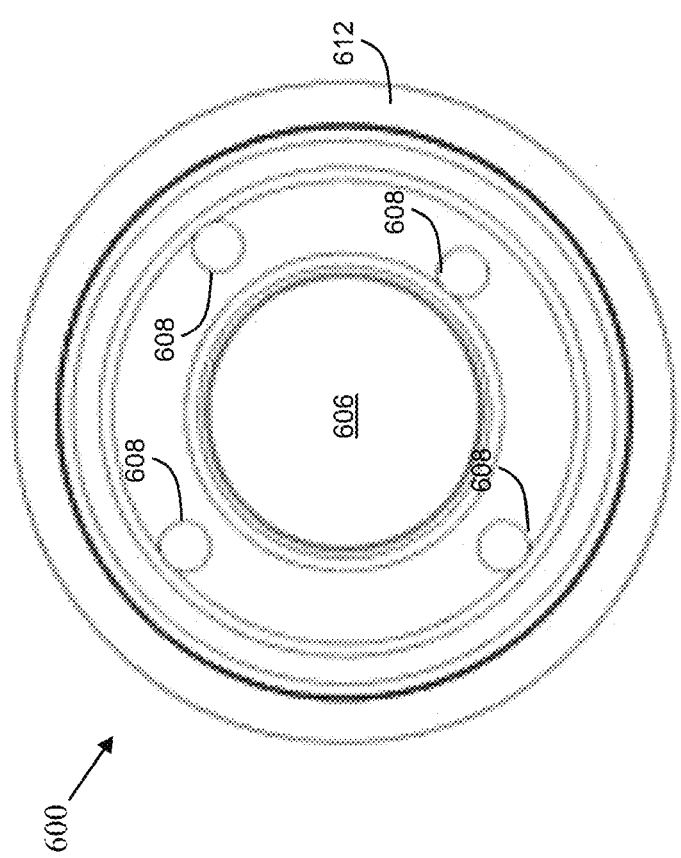
FIG. 7 is a diagram illustrating a front view of the patient reference device, as shown in FIGS. 6A and 6B, comprising a cover and a housing, for performing a medical procedure by way of the navigation system, in accordance with an embodiment of the present disclosure.

Referring to FIG. 7, this diagram illustrates, in a front view, the patient reference device 600, as shown in FIGS. 6A and 6B, comprising a cover 612 and a housing 602, for performing a medical procedure by way of the navigation system 200, in accordance with an embodiment of the present disclosure. The patient reference device 600 has a drape attached, wherein the drape has a window with a plurality of tracking markers 608, such as tracking spheres.

Figure 8:
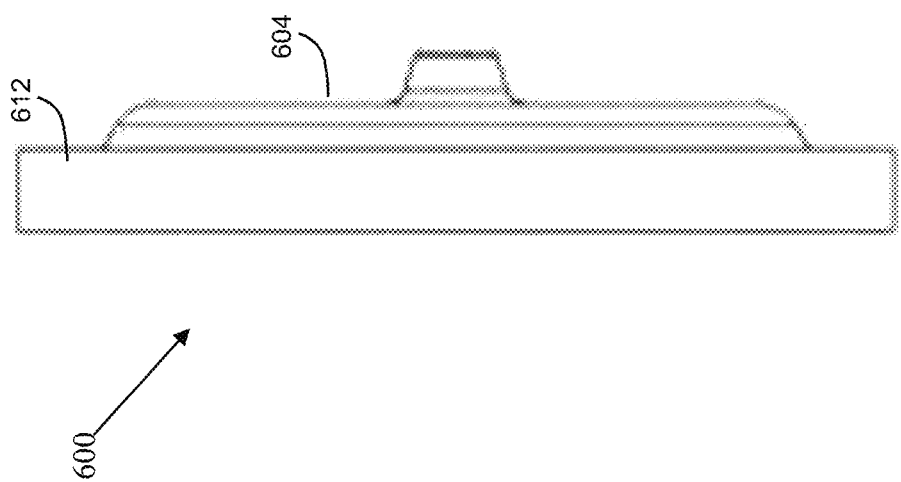
FIG. 8 is a diagram illustrating a side view of the patient reference device, as shown in FIGS. 6A and 6B, comprising a cover and a housing, for performing a medical procedure by way of the navigation system, in accordance with an embodiment of the present disclosure.

Referring to FIG. 8, this diagram illustrates, in a side view, the patient reference device 600, as shown in FIGS. 6A and 6B, comprising a cover 612 and a housing 602, for performing a medical procedure by way of the navigation system 200, in accordance with an embodiment of the present disclosure. The patient reference device 600 is configured for attaching a drape (not shown).

Referring back to FIGS. 6A, 6B, 7, and 8, the patient reference device 600 comprises a housing 602 having a back side 604 and a front side 606, by example only, at least three tracking markers 608 are attached to the front side 606 of the housing 602. In another example, four or more tracking makers 608 may be used. The tracking markers 608 each comprise a top 614, generally on the opposite side in relation to a portion of the tracking markers 608 that attach to the housing 602. While an example of either three or four tracking markers 608 is provided, any number of tracking markers 608 may be used for a particular application and is encompassed by the present disclosure. In one example, only one or two tracking markers may be used. In another example, the tracking markers 608 comprise passive reflective tracking spheres or active infrared (IR) markers that may be visible to a tracking camera, such as the tracking camera 307 of the navigation system 200. In another example, the tracking markers 608 may be active light emitting diodes (LEDs) or a graphical pattern printed on a three dimensional (3-D) structure used by a vision system such as the tracking camera to acquire 6 degrees of freedom (DOF).

Still referring back to FIGS. 6A, 6B, 7, and 8, the housing 602 is generally disc shaped; however, any suitable shaped housing or frame may be used for a particular application and is encompassed by the present disclosure. In some examples, the housing 602 comprises a solid member, either square shaped or disc shaped and the frame may further have superfluous material removed that is not important to the structural integrity of the housing, e.g., the housing comprises generally square shape or a disc shape with holes formed therein. In one example, the housing 602 comprises a metal, such as machined aluminum, blasted with aluminum oxide, e.g., 180-grit, and then hard anodized. Both the blasting and anodization processes provide a matte finish of the housing 602 whereby unwanted reflection is minimized to facilitate tracking by the tracking camera. Naked metallic surfaces or even plastic sometimes lead to poor accuracy for camera based tracking systems due to the presence of reflection, which can be further magnified with the use of a plastic drape on the patient reference 600. In the present disclosure, the exemplary blasted and anodized aluminum finish improves tracking performance of the tracking camera without degrading accuracy. While one example of a suitable finish for the housing 602 is provided, any suitable finish of low reflectivity may be used to meet the criteria of a particular implementation. In another example, the housing 602 comprises any suitable type of plastic or metal.

Still referring back to FIGS. 6A, 6B, 7, and 8, the housing 602 extends along the back side 604 of the housing 602. The housing 602 further extends beyond a horizontal plane defined by the tops 614 of the tracking markers 608. The housing terminates at an edge 610. In one example, the edge 610 may be substantially continuous, such as forming a shape such as a circle, a square, an oval, or a rectangle in one plane. A sterile cover 612 may be attached to the substantially continuous edge 610 of the housing 602 for covering the housing 602 and the tracking markers 608. In one example, the housing 602 may be generally domed shaped with a flattened back side and the sterile cover 612 may be round. However, the housing 602 may also be pyramid shaped, cone shaped, dome shaped, dish shaped, or of any other suitable shape to meet the design criteria of a particular application. The shape of the sterile cover 612 is then designed to mate appropriately with the shape of the housing 602.

Still referring back to FIGS. 6A, 6B, 7, and 8, the housing 602 of the patient reference device 600 may be attachable to an arm, such as the patient reference arm 500, as shown in FIG. 5. The patient reference arm 500 may be attachable by way of the mounting bolt 510 to a Mayfield head holder or any other head securing device, such that the patient reference device 600 is rigidly attached in a static location relative to the head securing device. In one example, the continuous edge 610 may have a seal located on the continuous edge 610 for forming a seal between the housing 602 and the sterile cover 612. In one example, the seal may be attached to the continuous edge 610 using any suitable adhesive. The sterile cover 612 may further have a sterile drape attached thereto for covering the housing 602 and a patient reference arm 500 attached to and holding the patient reference device 600 in position.

Still referring back to FIGS. 6A, 6B, 7, and 8, for example, a lens 616 of the sterile cover 612 comprises a substantially transparent plastic material that is easily sterilizable and has optical properties that are controllable, wherein infrared light that is transmitted through the lens 616 of the sterile cover 612 is reflected from the tracking markers 608 and is transmitted back through the lens 616 of sterile cover 612 without excessive diffraction which would otherwise be problematic for the tracking camera, e.g., the tracking camera 307, that is monitoring the tracking markers 608. In one example, the sterile cover 612 comprises glass, quartz, or sapphire. In some examples, the lens 616 of the sterile cover 612 may have additional optical properties, such as that of a band-pass filter that allows transmission of infrared light, but blocks any suitable portion of the frequency spectrum on each side of the IR pass band. In another example, the lens 616 of the sterile cover 612 may have the optical properties of a low-pass or a high-pass optical filter. Alternatively, the optical properties of the lens 616 of the sterile cover 612 are optimized for passing visible light or only visible light in the example where a graphical pattern is printed on a structure. While some examples have been given for possible optical filter characteristics, any suitable optical filter may be applied to the lens 616 for a particular application.

Still referring back to FIGS. 6A, 6B, 7, and 8, the patient reference device 600 further comprises at least one sensor (not shown) attached thereto for providing a signal to the navigation system, such as the navigation system 200, as shown in FIG. 2, which may include the control and processing unit 300, as shown in FIG. 3. In one example, the sensor comprises an accelerometer, a force sensor, a gyroscope, a magnetometer, a strain gauge, or any other suitable sensor. The sensor may be either attached to the exterior of the housing 602 or embedded in or integrated into the housing 602. In one example, the patient reference device 600 may have a triaxial accelerometer attached thereto for sensing acceleration in any of the X, Y, and Z directions and providing the signal generated by the accelerometer to the control and processing unit 300. For example, the accelerometer mounted on the patient reference device 600 comprises one of the external I/O devices 344, as shown in FIG. 3. The control and processing unit 300 is programmable, e.g., via one of the processing engines 370, to monitor signals from the accelerometer after the patient reference device 600 has been put into position and registered during the registrations steps, as indicated by blocks 406 and 408, as shown in FIG. 4A.

Still referring back to FIGS. 6A, 6B, 7, and 8, the control and processing system 300 is configured to receive data from the accelerometer that indicates an acceleration of the patient reference device 600 or the patient reference arm 500, e.g., by way of jolting, perhaps by one of the medical staff accidentally hitting or kicking the patient reference device 600 or the patient reference arm 500. When the acceleration, indicated by the accelerometer, exceeds a threshold such that enough force was generated that could have thrown the patient reference device from its proper fixed position, the control and processing system 300 responds accordingly. For example, the control and processing system 300 transmits data to a display device 311 which displays a warning to the operator, prompting checking the position of the patient reference device 600. In another example, the control and processing system 300 may simply require the operator of the system 200 to reregister the patient reference device 600 for ensuring that the position of the patient reference device 600 relative to the head holding device is properly perceived by the navigation system 200.

Figure 9A:
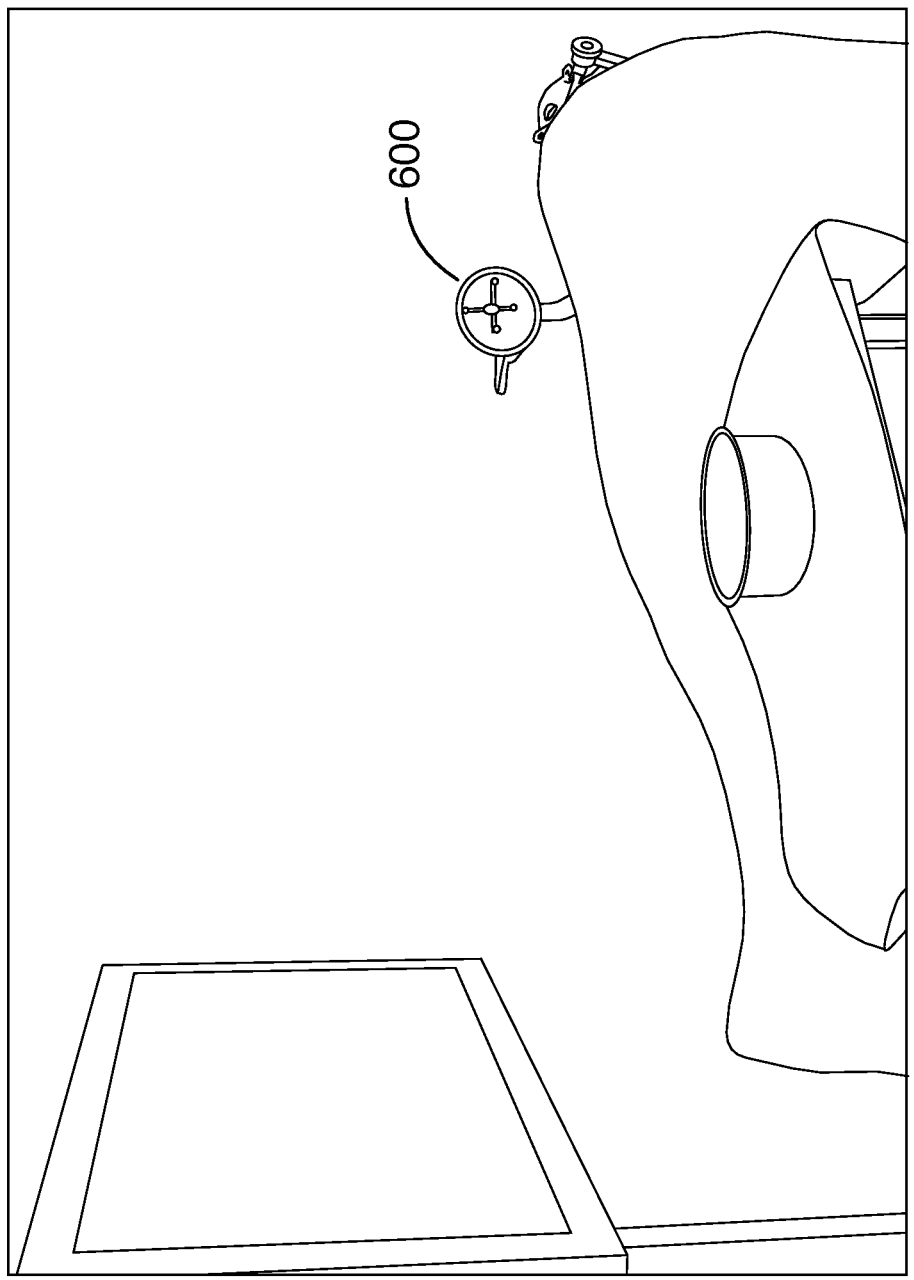
FIG. 9A is a diagram illustrating a perspective view of the patient reference device, as shown in FIGS. 6A and 6B, comprising a cover and a housing, for performing a medical procedure by way of the navigation system in a medical environment, such as an operating room, in accordance with an embodiment of the present disclosure.

Referring to FIG. 9A, this diagram illustrates, in a perspective view, the patient reference device 600, as shown in FIGS. 6A and 6B, comprising a cover 612 and a housing 602, for performing a medical procedure by way of the navigation system 200 in a medical environment, such as an operating room OR, in accordance with an embodiment of the present disclosure. The patient reference device 600 is shown attached to an arm 500 that fixes the patient reference device 600 in position at the head end of a medical bed for performing a medical procedure in an operating room OR. Several aspects of the navigation system 200, as described in relation to FIG. 2, are shown surrounding the medical bed.

Figure 9B:
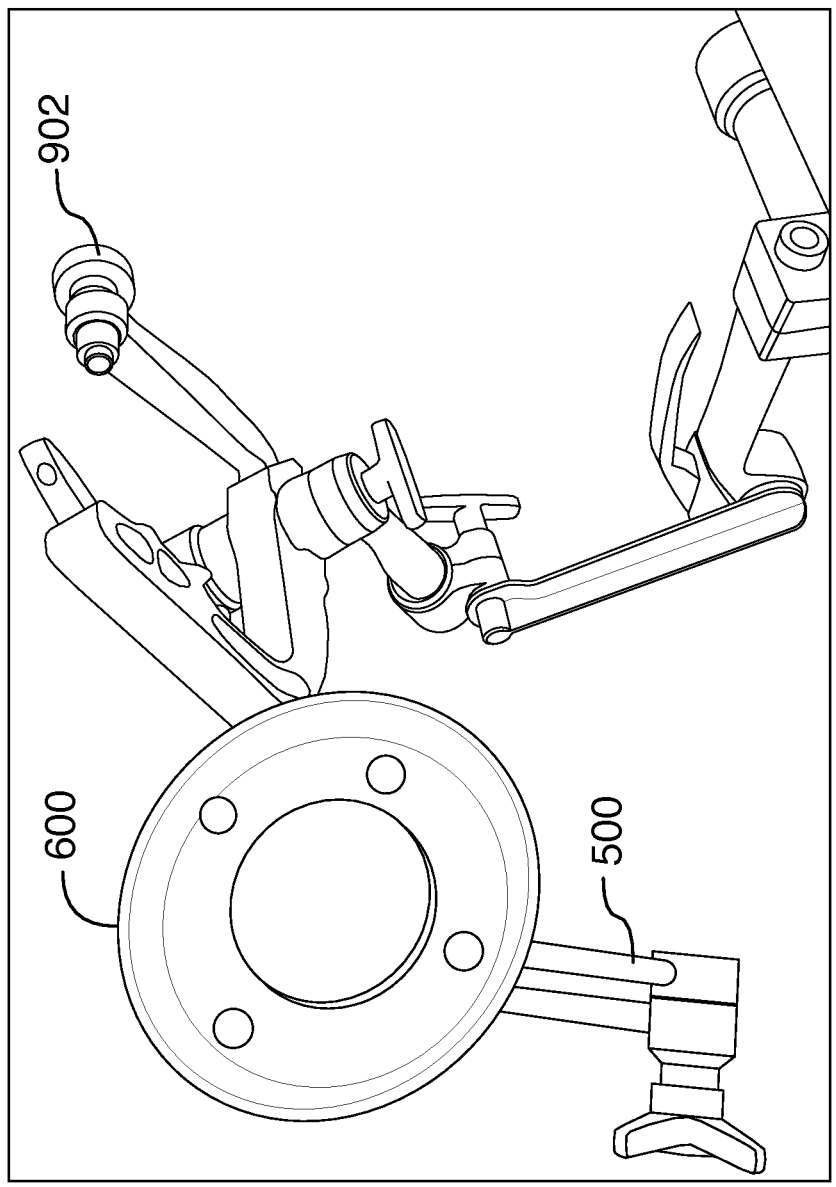
FIG. 9B is a diagram illustrating a perspective view of the patient reference device, as shown in FIGS. 6A and 6B, comprising a cover and a housing, coupled with the arm, as shown in FIG. 5, for performing a medical procedure by way of the navigation system, in accordance with an embodiment of the present disclosure.

Referring to FIG. 9B, this diagram illustrates, in a perspective view, the patient reference device 600, as shown in FIGS. 6A and 6B, comprising a cover 612 and a housing 602, coupled with the arm 500, as shown in FIG. 5, for performing a medical procedure by way of the navigation system 200, in accordance with an embodiment of the present disclosure. The patient reference device 600 is installable in relation to the arm 500.

Figure 9C:
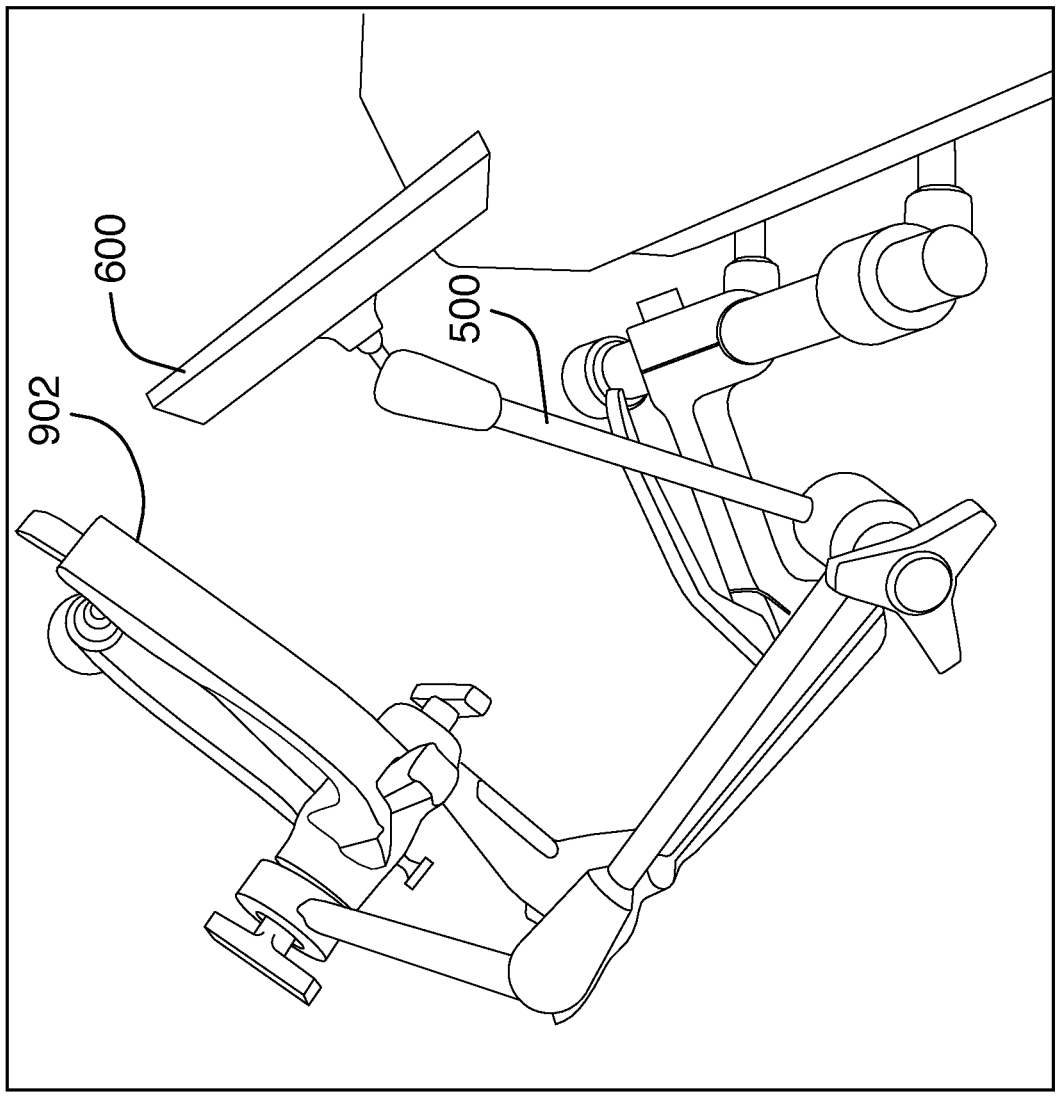
FIG. 9C is a diagram illustrating another perspective view of the patient reference device, as shown in FIGS. 6A and 6B, comprising a cover and a housing, coupled with the arm, as shown in FIG. 5, for performing a medical procedure by way of the navigation system, in accordance with an embodiment of the present disclosure.

Referring to FIG. 9C, this diagram illustrates, in another perspective view, the patient reference device 600, as shown in FIGS. 6A and 6B, comprising a cover 612 and a housing 602, coupled with the arm 500, as shown in FIG. 5, for performing a medical procedure by way of the navigation system 200, in accordance with an embodiment of the present disclosure. The patient reference device 600 is installable in relation to the arm 500.

Figure 9D:
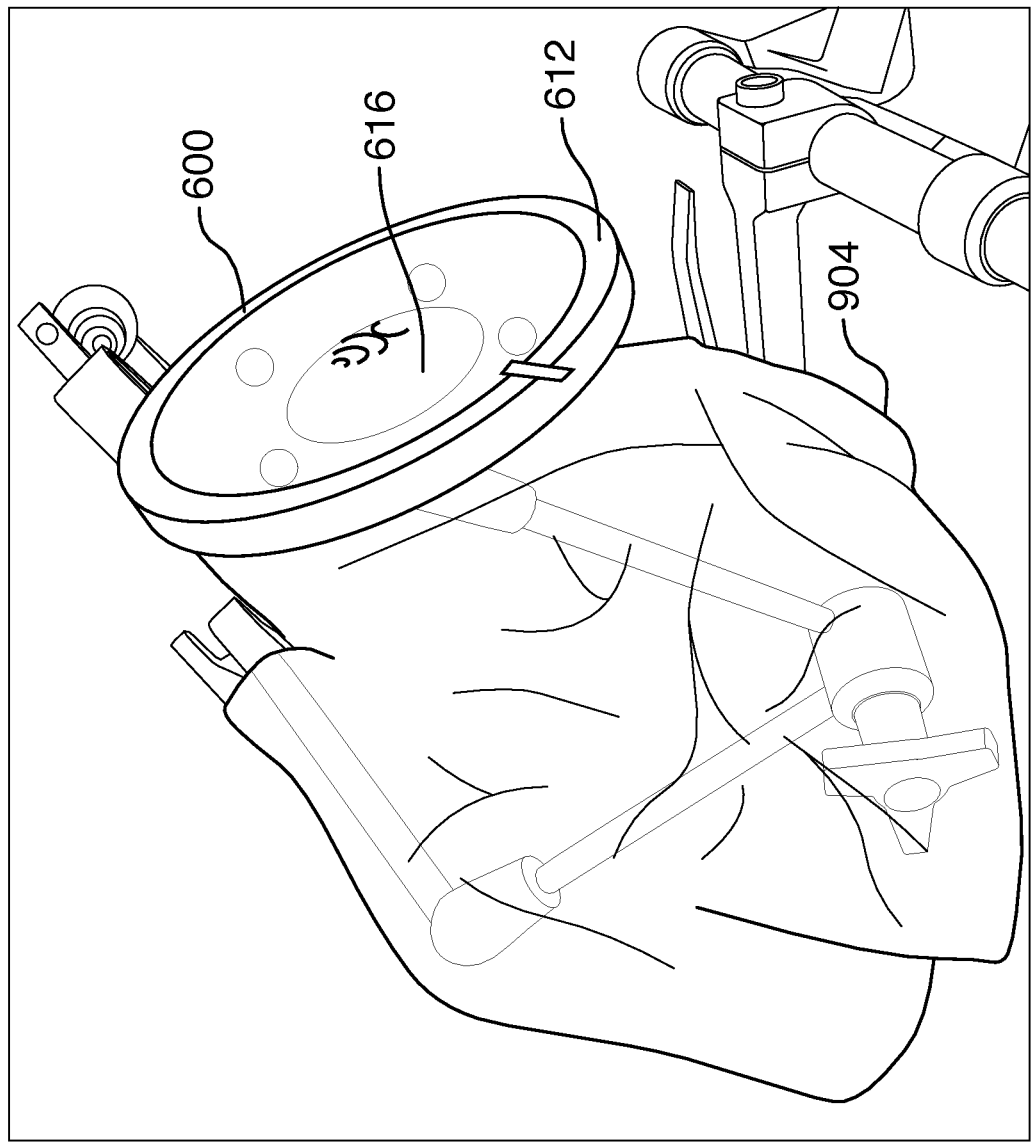
FIG. 9D is a diagram illustrating a perspective view of the patient reference device, as shown in FIGS. 6A and 6B, comprising a cover and a housing, coupled with the arm, as shown in FIG. 5, in use with a sterile drape, for performing a medical procedure by way of the navigation system, in accordance with an embodiment of the present disclosure.

Referring to FIG. 9D, this diagram illustrates, in a perspective view, the patient reference device 600, as shown in FIGS. 6A and 6B, comprising a cover 612 and a housing 602, coupled with the arm 500, as shown in FIG. 5, in use with a sterile drape 904, for performing a medical procedure by way of the navigation system 200, in accordance with an embodiment of the present disclosure. The patient reference device 600 is installable in relation to the arm 500 and the sterile drape 904.

Figure 9E:
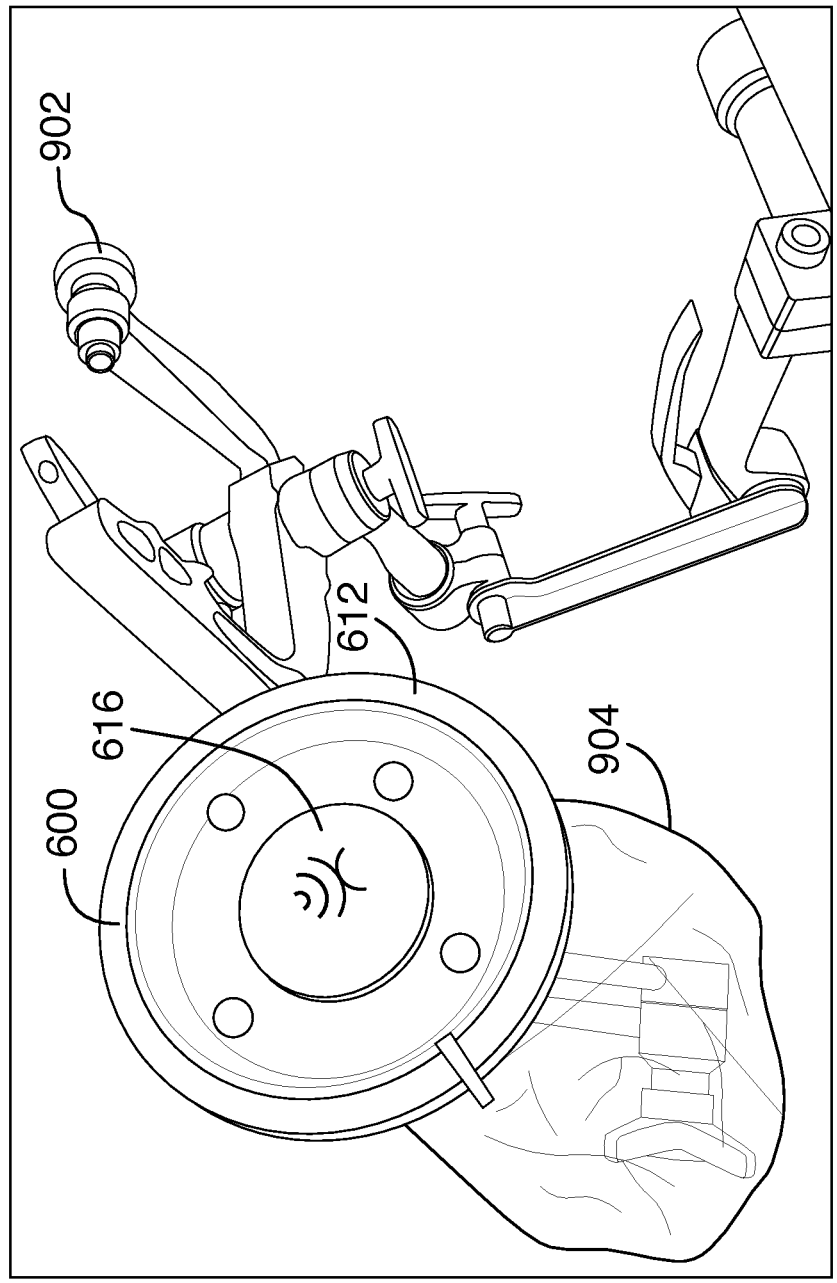
FIG. 9E is a diagram illustrating another perspective view of the patient reference device, as shown in FIGS. 6A and 6B, comprising a cover and a housing, coupled with the arm, as shown in FIG. 5, in use with a sterile drape, for performing a medical procedure by way of the navigation system, in accordance with an embodiment of the present disclosure.

Referring to FIG. 9E, this diagram illustrates, in another perspective view, the patient reference device 600, as shown in FIGS. 6A and 6B, comprising a cover 612 and a housing 602, coupled with the arm 500, as shown in FIG. 5, in use with a sterile drape 904, for performing a medical procedure by way of the navigation system 200, in accordance with an embodiment of the present disclosure. The patient reference device 600 is installed in relation to the arm 500 and the sterile drape 904.

Referring back to FIGS. 9B-9D, the patient reference device 600 is shown attached to an arm, such as the patient reference arm 500. The mounting bolt 504 of the arm 500 attaches the arm 500 to a Mayfield clamp 902, or any other suitable head holding device for restraining the head of a patient. Since the patient reference device 600 is, therefore, rigidly attached to the Mayfield clamp 902, the patient reference device 600 is located in a fixed location relative to the patient's head and, therefore, relative to the surgical site of interest.

Referring back to FIGS. 9D-E, the patient reference device 600 has a sterile drape 904 attached, covering the arm 500 and other components that are typically not sterilized prior to the medical procedure to be performed. The sterile cover 612 and the lens 616 are shown in position attached to the continuous edge 610 of the patient reference device 600. By example only, the present disclosure encompasses a kit comprising the patient reference device 600, wherein the components are configured for assembly by an end user, such as a hospital or medical clinic. The kit comprises the housing 602, the cover 612, the arm 500 having mounting bolt 504 or other suitable connecting mechanism for attaching to a Mayfield clamp, the tightening screw and/or knob 502, the tracking markers 608, and/or the sterile drape 904.

Figure 10:
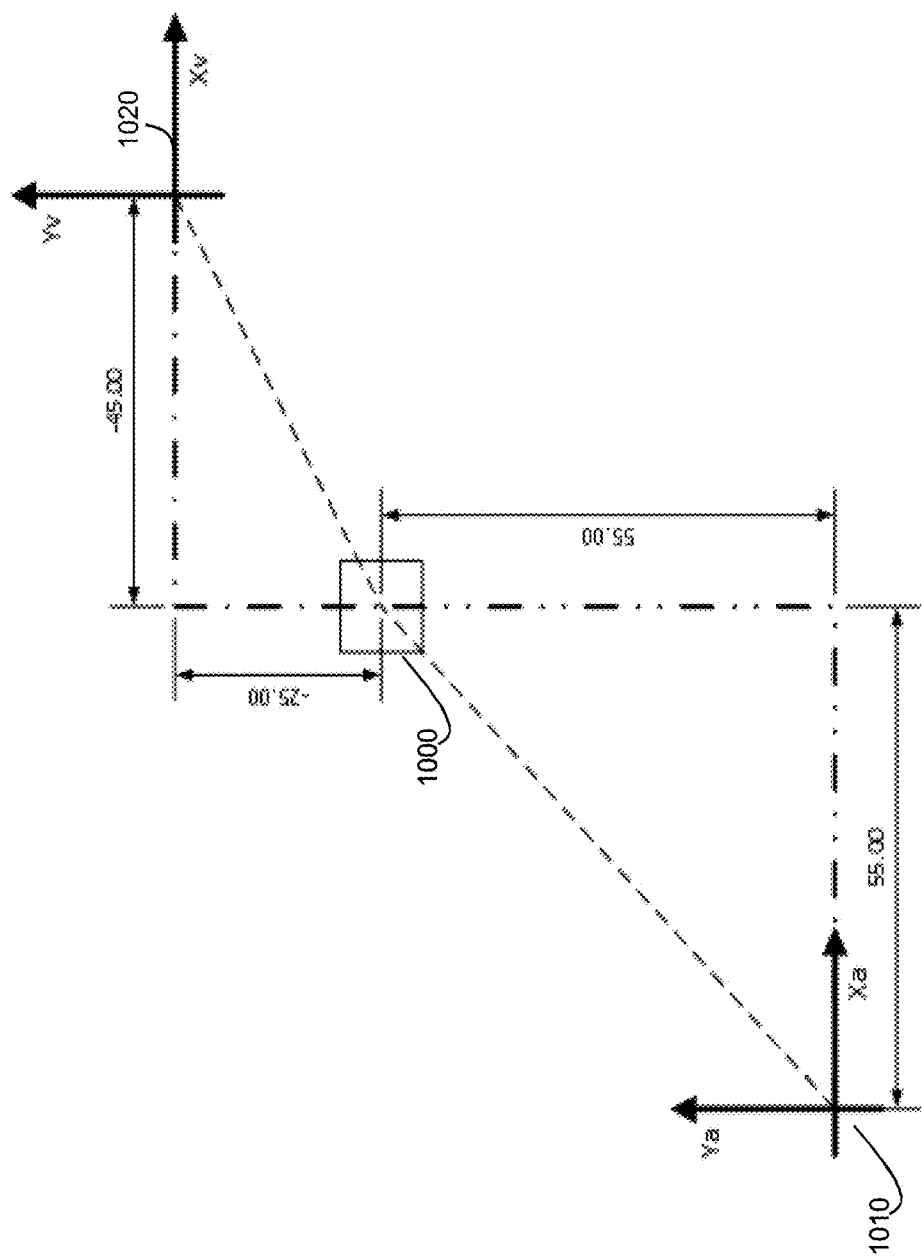
FIG. 10 is a schematic diagram illustrating relative orthogonal relationships of at least one patient reference device, such as among at least one patient reference device, each having a plurality of patient reference markers, used in the method of registering a patient, as shown in FIG. 4B, for performing a medical procedure by way of the navigation system, in accordance with an embodiment of the present disclosure.

Referring to FIG. 10, this schematic diagram illustrates relative orthogonal relationships of at least one patient reference device, such as among at least one patient reference device 600, each having a plurality of patient reference markers, used in the method of registering a patient, as shown in FIG. 4B, for performing a medical procedure by way of the navigation system 200, in accordance with an embodiment of the present disclosure. A registration process, similar to that which may be used in part in block 456 of FIG. 4B, is shown for creating a common coordinate space composed of amalgamated virtual and actual coordinate spaces. The common coordinate space comprises both an actual coordinate space and a virtual coordinate space, wherein the actual coordinate space contains actual objects (or subjects) existing in space, and wherein the virtual coordinate space contains virtual objects (or subjects) generated in a virtual space. The common coordinate space, containing the actual objects (or subjects) and the virtual objects (or subjects), is provided by the systems and methods of the present disclosure as follows.

Still referring to FIG. 10, in order to form a common coordinate space, comprising an amalgamation of the virtual coordinate space and the actual coordinate space, the systems and methods of the present disclosure involve associating or amalgamating these two spaces with a "common reference coordinate" having a defined position locatable in both the actual and virtual coordinate spaces. An example of such a common reference coordinate 1000, an actual coordinate space origin 1010, and a virtual coordinate space origin 1020 are shown. Once the common reference coordinate position is acquired in both spaces, the spaces can be used to correlate the position of any point in one coordinate space in relation to the other coordinate space. The correlation is determined by equating the locations of the common reference coordinate in both spaces and by solving for an unknown translation variable for each degree of freedom defined in the two coordinate spaces. These translation variables are used to transform a coordinate element of a position in one space to an equivalent coordinate element of a position in the other space. An example correlation is derived from the diagram, as shown in FIG. 10, depicting a two dimensional coordinate space. In FIG. 10, the common reference coordinate 1000 position is determined relative to the actual coordinate space origin 1010 and the virtual coordinate space origin 1020. The common reference coordinates positions can be derived from the diagram as follows:

$(X_{cra}, Y_{cra}) = (55, 55)$ and $(X_{crv}, Y_{crv}) = (-25, -45)$, wherein the subscript "cra" denotes the common reference coordinate 1000 position relative to the actual coordinate space origin 1010 and the subscript "crv" denotes the common reference coordinate 1000 position relative to the virtual coordinate space origin 1020.

Still referring to FIG. 10, utilizing a translation equation describing any points $(Y_a, X_a)$ and $(Y_v, X_v)$, wherein the subscript "a" denotes the coordinates of a point relative to the actual coordinate space origin 1010, and the subscript "v" denotes the coordinate of a point relative to the virtual coordinate space origin 1020, the individual coordinates from each space are equated to solve for translation variables (YT, XT), and wherein the subscript "T" denotes the translation variable as follows:

$Y_a = Y_v + Y_T$ $X_a = X_v + X_T.$

Still referring to FIG. 10, substituting the derived values of our points, for the translation variable is solvable as follows:

$55 = -45 + Y_T$ $100 = Y_T$ and $55 = -25 + X_T$ $80 = X_T.$

Still referring to FIG. 10, utilizing this translation variable, any point, i.e., (Yv, Xv), in the virtual coordinate space may be transformed into an equivalent point in the actual coordinate space through the two transformation equations as follows:

$Y_a = Y_v + 100$ and $X_a = X_v + 80.$

Noted is that these equations can be rearranged to transform any coordinate element of a position from the actual coordinate space into an equivalent coordinate element of a position in the virtual coordinate space as well, in accordance with an embodiment of the present disclosure.

Still referring to FIG. 10, the foregoing transformation allows both the virtual and actual objects', or subjects', respective positions to, therefore, be defined in both the actual and virtual coordinate spaces simultaneously. Once the correlation is determined, the actual and virtual coordinate spaces become coupled, or associated, and thereby provide a common coordinate space for registering virtual and actual objects, or subjects. Noted is that these virtual and actual object, or subjects, can be superimposed in the common coordinate space, e.g., they can occupy the same coordinates simultaneously.

Still referring to FIG. 10, in accordance with an embodiment of the present disclosure, the navigation system 200 further comprises a three-dimensional (3-D) surface scanner system, comprising a 3-D scanner 309, such as a handheld 3-D surface scanner, e.g., a 3-D scanner handheld, for obtaining a full or nearly full array scan of a patient's surface can be achieved, in contrast to a one-dimensional (1-D) line or a two-dimensions (2-D) grid of point depths with the related art conventional approaches. This embodiment of the present disclosure, using the 3-D scanner 309, obtains point information having an order of magnitude that is greater than that achieved via the surface tracing methods used in related art conventional approaches. The 3-D scanner 309 provides data, such as relating to a dense point cloud. The dense point cloud is mapped to the extracted surface of the MR/CT volumetric scan data, e.g., the pre-operative ("pre-op") image data, to register the patient's physical position to the volumetric data. The navigation system 200 further comprises a tool that is visible to both the tracking system 321 and the 3-D scanner 309, whereby visibility is provided to the point cloud data, whereby a transformation of data between that of the tracking system's camera space and that of the 3-D scanner space is identified, and whereby the point cloud provided by the 3-D scanner 309 and the tracking system 321 is registrable to the patient space. A data transformation, such as described in connection with FIG. 10 or derivatives thereof, is effected for patient registration, in accordance with embodiments of the present disclosure.

Still referring to FIG. 10, in accordance with an embodiment of the present disclosure, a tracking tool is at least partially optimized for visibility and tracking by both the tracking system 321 and a 3-D scanner system, such as a 3-D scanner 309. In one example, the 3-D scanner 309 may be a colour 3-D scanner. The 3-D scanner 309 may be used to collect a colour point cloud which is defined in the patient space. To determine a transformation mapping between the tracking system 321 and the patient space, the tracking tool may be identifiable in both spaces. While there may be guidelines for tool design compatibility with the tracking system 321, no such rules exist for creating targets for extraction within point clouds. In one example, a cross-compatible tool may be designed using three retro-reflective circular targets placed at unique distances from one another on a single rigid plane. Each target may include an IR retro-reflective sphere for visibility by the tracking system 321. Three dimensional features may be provided on the tracking tool which enables straight forward extraction from the output point cloud collected from the 3-D scanner 309.

Figure 11:
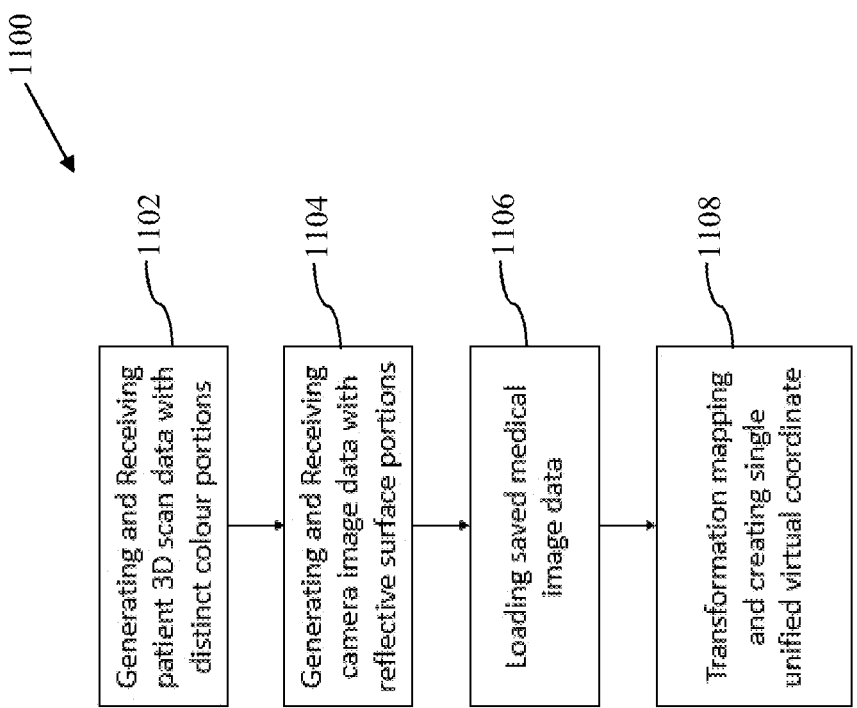
FIG. 11 is a flow chart illustrating a method of registering a patient, as shown in FIG. 10, via at least one patient reference device, such as among at least one patient reference device, each having a plurality of patient reference markers for performing a medical procedure by way of the navigation system, in accordance with an alternative embodiment of the present disclosure.

Referring to FIG. 11, this flow chart illustrates a method 1100 of registering a patient, as shown in FIG. 10, via at least one patient reference device, such as among at least one patient reference device 1300 (FIG. 13) and the like, each having a plurality of patient reference markers 1304 and the like, for performing a medical procedure by way of the navigation system 200, in accordance with an alternative embodiment of the present disclosure. The method 1100 is performed to register a patient for a medical procedure with a medical navigation system, such as the medical navigation system 200, using a patient reference device, such as the device 600, the device 1300, and the like, visible by both a 3-D scanner system, such as a 3-D scanner 309, of the medical navigation system 200 and a camera, such as the camera 307, of the medical navigation system 200. The method 1100 may be controlled and/or executed, for example by the processor 302 of the control and processing unit 300 of the medical navigation system 200.

Still referring to FIG. 11, the method 1100 of registering a patient comprises: generating and receiving 3-D scan data from the 3-D scanner 309 that is representative of a 3-D scan of at least a portion of the patient 202, as indicated by block 1102. The 3-D scan comprises distinct identifiable portions of the patient reference device 1300 that are visible by the 3-D scanner 309. In one example, the distinct identifiable portions comprise at least one 3-D shape located on a surface of the patient reference device 1300. In another example, the distinct identifiable portions comprise three-dimensional indicators or distinct color portions. While these are examples, the scan data need not be 3-D scanned data with distinct color portions; and other suitable forms of data may be used and are encompassed by the present invention.

Figure 13:
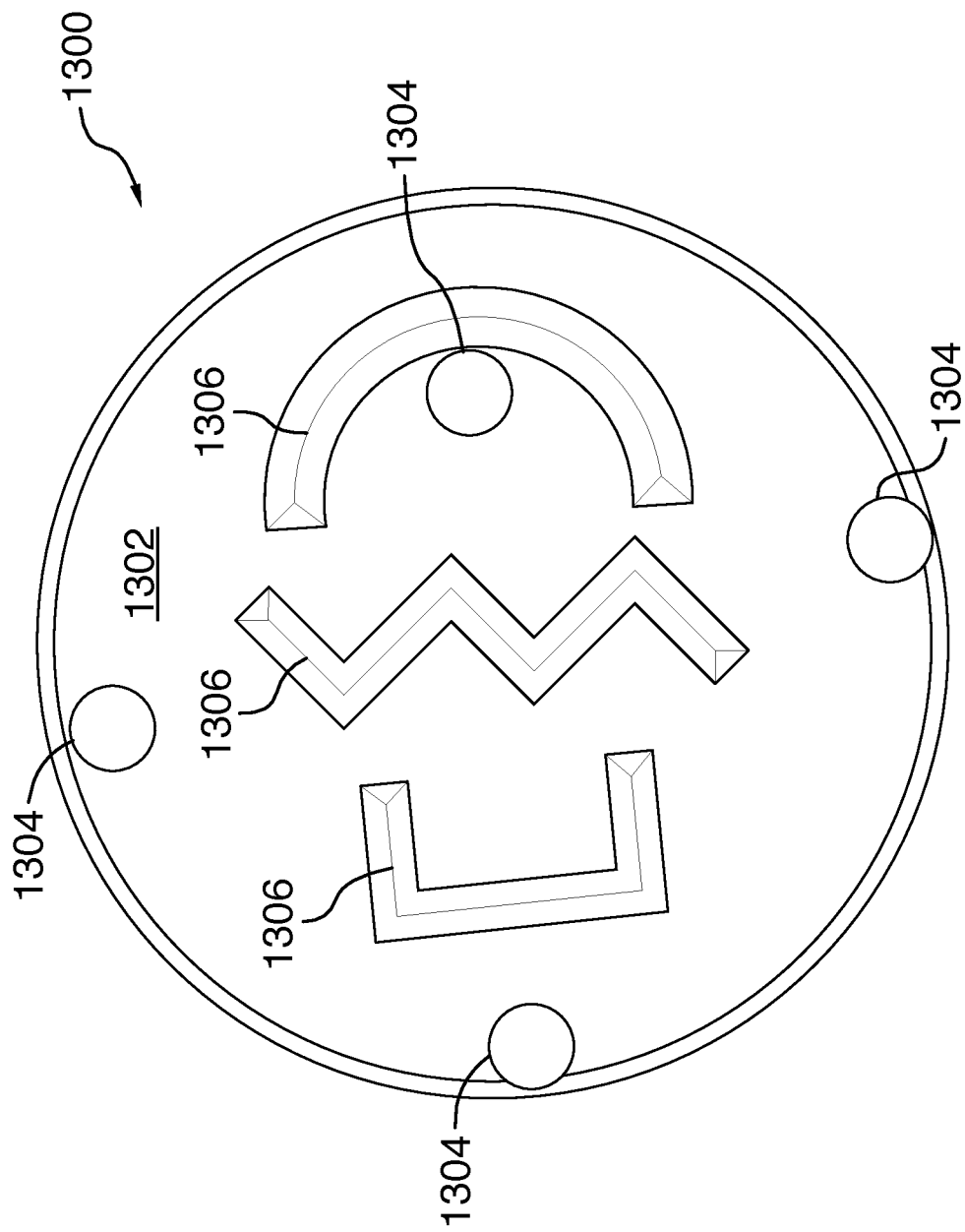
FIG. 13 is diagram illustrating a top view of a patient reference device, in accordance with an embodiment of the present disclosure.

Still referring to FIG. 11, the method 1100 of registering a patient further comprises: generating and receiving image data from the camera 307, as indicated by block 1104. In one example, the image data may include reflective surface portions of the patient reference device 1300 visible by the camera 307. In one example, the reflective surface portions comprise the reflective markers 1304 (FIG. 13). While reflective markers 1304 are used as an example, any suitable type of markers may be used according to a particular application and are encompassed by the present disclosure.

Still referring to FIG. 11, the method 1100 of registering a patient further comprises: loading saved medical image data, as indicated by block 1106. The saved medical data comprises pre-operative image data, such as the pre-op image data 354, saved during a previous scan of at least a portion of the patient 202. The pre-op image data 354 comprises data from computerized tomography (CT) images, magnetic resonance imaging (MRI) images, positron emission topography (PET) images, contrast-enhanced CT images, X-ray images, ultrasound images, or any other suitable medical imaging source.

Still referring to FIG. 11, the method 1100 of registering a patient further comprises performing a transformation mapping to create a single unified virtual coordinate space based on the 3-D scan data, the image data, and the medical image data, as indicated by block 1108. In one example, the performing the transformation generally comprises the registration method described in connection with FIG. 10. In another example, performing the transformation mapping comprises using a surface matching approach using a 3-D scanner point cloud based on the 3-D scan data and at least one of MR and CT coordinates. In another example, using a navigation system 200, comprising a tracking system 321 and a camera 307, performing the transformation mapping further comprises registering the tracking system 321 to create a single unified virtual coordinate space for the 3-D scanner point cloud, at least one of the MR and CT coordinates, and the image data from the tracking system 321. However any suitable or yet to be developed transformation process may be applied and is encompassed by the present disclosure. In the method 1100, the steps generally indicated by blocks 1102, 1104, 1106, and 1108 may be performed in any suitable order, including concurrently; and any such order is encompassed by the present disclosure. An alternative order of performing the steps of method 1100 are described in connection with FIG. 12.

Figure 12:
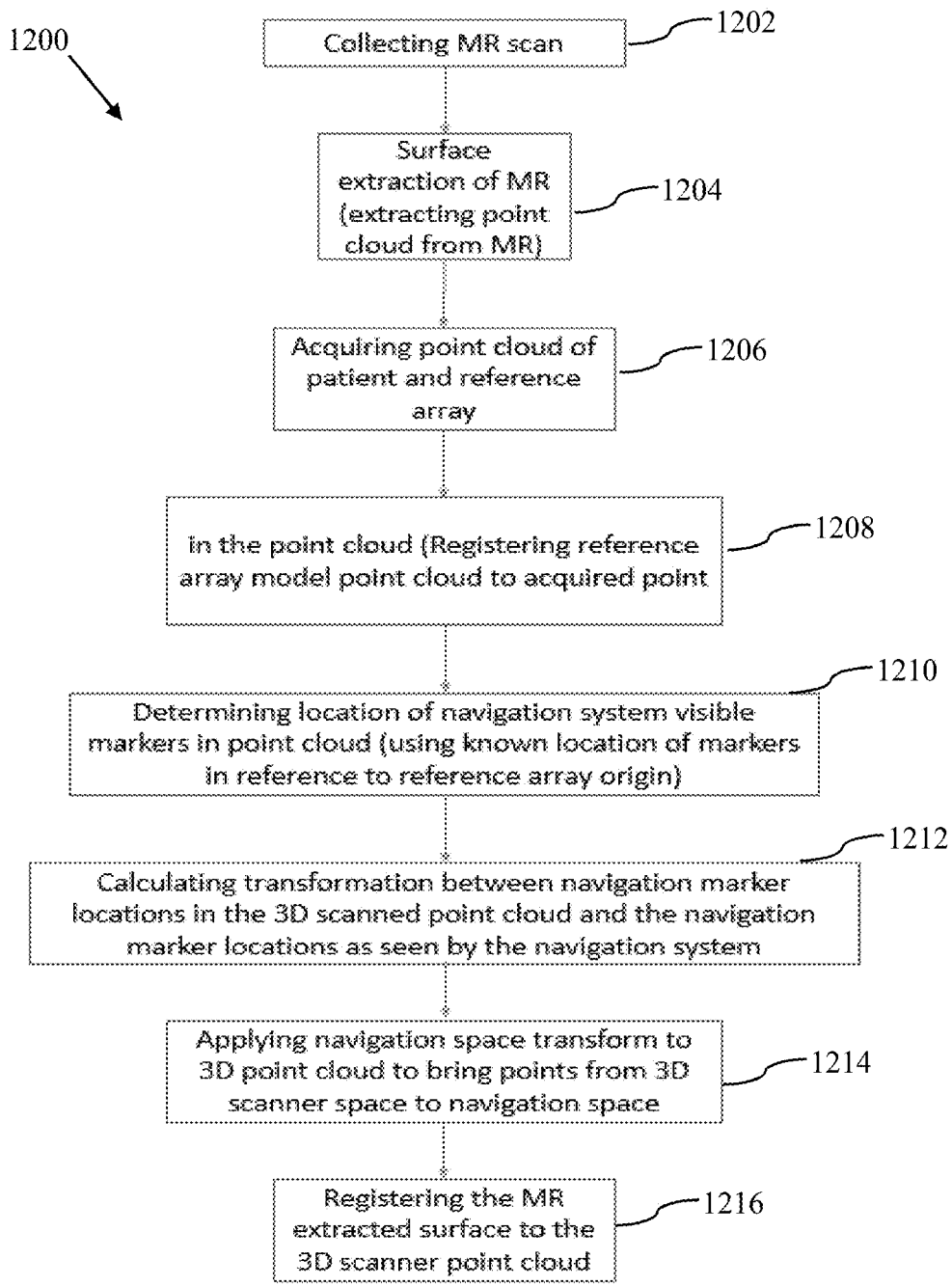
FIG. 12 is a flow chart illustrating a method of registering a patient, such as shown in FIGS. 10 and 11, via at least one patient reference device, such as among at least one patient reference device, each having a plurality of patient reference markers, for performing a medical procedure by way of the navigation system, in accordance with another alternative embodiment of the present disclosure.

Referring to FIG. 12, this flow chart illustrates a method 1200 of registering a patient 202, such as shown in FIGS. 10 and 11, via at least one patient reference device, such as among at least one patient reference device 1300, each having a plurality of patient reference markers 1304, for performing a medical procedure by way of the navigation system 200, in accordance with another alternative embodiment of the present disclosure. The method 1200 comprises collecting image scan data, as indicated by block 1202, wherein collecting image scan data comprises a step of loading saved medical image data, as indicated by block 1106, in the method 1100. Collecting image scan data, as indicated by block 1202, comprises collecting any 3-D volumetric image scan data, such as magnetic resonance (MR) image scan data, CT image scan data, 3-D ultrasound image scan data, and any other suitable type of scanned image data according to any particular application.

Still referring to FIG. 12, the method 1200 further comprises surface-extracting using the image scan data, thereby generating a point cloud, as indicated by block 1204. In the method 1100, the step of performing transformation mapping, as indicated by block 1108, comprises the surface-extracting using the image scan data, thereby generating a point cloud, as indicated by block 1204. The method 1200 further comprises generating a point cloud of the patient 202 and a reference array, e.g., in relation to the device 1300, as indicated by block 1206, wherein generating a point cloud comprises using data generated by the 3-D scanner 309, such as a handheld 3-D scanner 309.

Still referring to FIG. 12, the method 1200 further comprises identifying the location of the reference array in the point cloud, as indicated by block 1208. In one example, the medical navigation system 200 is configured to store data to facilitate recognition of the reference array, such as the patient reference device 1300, in an image scanned by the 3-D scanner 309. In one example, the reference array comprises three-dimensional features that are recognizable in an image scanned by the 3-D scanner 309, thereby allowing the medical navigation system 200 to find the reference array in the image by way of the 3-D features being in locations known in reference to some features, such as the reflective markers 1304, and visible to the navigation system 200.

Still referring to FIG. 12, the method 1200 further comprises determining the location of the navigation system visible markers in the point cloud, as indicated by block 1210. In one example, determining the location of the reference array, e.g., as indicated by block 1208, facilitates finding the visible markers 1304 on the reference array by the medical navigation system 200 as the reference array has a spatial configuration known by the medical navigation system 200. The method 1200 further comprises: calculating the transformation between the navigation marker locations in the 3-D scanned point cloud and the navigation marker locations by way of the navigation system 200, as indicated by block 1212; applying the navigation space transformation to the 3-D point cloud to bring points from the 3-D scanner 309 space into the navigation space, as indicated by block 1214; registering the patient image extracted surface to the 3-D scanner 309 point cloud; as indicated by block 1216.

Still referring to FIG. 12, in the method 1200, the step of performing transformation mapping, as indicated by block 1108, comprises at least one step, as indicated by blocks 1212, 1214, and 1216. In one example, in the methods 1100 and/or 1200, calculating the registration transformation comprises employing an Iterative Closest Point (ICP) approach, such as that detailed in "A Method for Registration of 3-D Shapes" by Paul J. Best and Neil D. McKay, IEEE Transactions on Pattern Analysis and Machine Intelligence, pp. 239-256, Vol. 14, No. 2, February 1992, hereby incorporated by reference in its entirety. Further, any suitable approach may be used depending on a particular application and is encompassed by the present disclosure. The method 1100 and the method 1200 are examples of methods that illustrate the context of using the patient reference device 1300 which is described in more detail below in connection with FIG. 13 and is encompassed by the present disclosure.

Referring to FIG. 13, this diagram illustrates, in a top view, a patient reference device 1300, in accordance with an embodiment of the present disclosure. In one example, the device 1300 may be referred to as a patient reference tool or patient reference device, similar to the device 600, as shown in FIG. 7. In one example, the patient reference device 1300 is used during a medical procedure. The device 1300 is visible by both the three-dimensional (3-D) scanner system, comprising the scanner 309, of the medical navigation system 200 and the tracking system 321 of the medical navigation system 200. In one example, a camera 307 of the tracking system 321 may be used to see the device 1300. The device 1300 comprises a rigid member 1302 and a plurality of navigation system visible identifiable features that are attached to the rigid member 1302. In one example, the navigation system identifiable features comprise reflective markers 1304. The plurality of reflective markers 1304 is visible by the tracking system 321, for example, by the camera 307.

Still referring to FIG. 13, the device 1300 further comprises a distinct identifiable portion 1306 visible by the 3-D scanner system 309 and a connector mechanism (not shown) attached to the rigid member 1302 to connect the device 1300 at a location. The connector mechanism comprises any suitable mechanism, such as the mechanisms described in connection with FIGS. 5 and 9A-E. The device 1300 may be in a field of view (FOV) of the 3-D scanner 309 and the tracking system 321 within a timeframe of the 3-D scan. In one example, the identifiable features comprise the reflective markers 1304; and the tracking system 321 comprises the camera 307. In another example, the identifiable features comprise magnetic coils; and the tracking system 321 comprises magnetic tracking sensors. In further alternate embodiments, the identifiable features comprise RFID tags or barcode tags; and the tracking system 321 comprises an RFID scanner or a barcode scanner. Similar to the reflective markers 1304, RFID and barcode tags are programmable with location data which, when read from a respective RFID or barcode scanner, transfer scanned data to the navigation system 200.

Still referring to FIG. 13, in one example, the device 1300 comprises at least three reflective markers 1304 mounted on a front side of the rigid member 1302. However, any suitable number of reflective markers 1304 may be used for a particular application and are encompassed by the present disclosure. In one example, the tracking markers 1304 comprise at least one of passive reflective tracking spheres, active infrared markers, active light emitting diodes, a graphical pattern, and any other suitable type of markers.

Still referring to FIG. 13, in another example, the rigid member 1302 comprises a substantially rigid and/or planar shape and a thickness or depth sufficient to accommodate the desired depth of the distinct identifiable portion 1306. The distinct identifiable portion 1306 comprises a three-dimensional indicator formed on the front side of the rigid member 1302. In another example, the distinct identifiable portion 1306 comprises a three-dimensional indicator formed on the back side of the rigid member 1302. In another example, the distinct identifiable portion 1306 comprises a three dimensional indicator formed on both the back side and the front side of the rigid member 1302. The three-dimensional indicator comprises at least one of an engraving and an etching in the rigid member 1302.

Still referring to FIG. 13, alternatively, the three-dimensional indicator comprises a raised surface portion on the front side of the rigid member 1302. In the example shown in FIG. 13, the three-dimensional indicator 1306 comprises three separate unique indicators; however, any suitable number of three-dimensional indicators may be used for a particular application and is encompassed by the present disclosure. While the rigid member 1302 is described, in one example, as comprising a planar configuration and having a front side and a backside, the rigid member 1302 comprises any suitable three-dimensional shape. For example, the rigid member 1302 comprises at least one configuration of a sphere, cone, pyramid, cube, prism, or even an amorphous shape.

Still referring to FIG. 13, in another embodiment, the device 1300 comprises a patient reference device. The rigid member 1302 may be referred to as a housing having a back side and a front side with a plurality of tracking markers 1304 attached to the front side of the housing. The device 1300 comprises a distinct identifiable portion 1306 including a three-dimensional indicator formed on the front side of the housing. The housing extends around the plurality of tracking markers 1304 and beyond a horizontal plane defined by tops or top portions of the plurality of tracking markers 1304. The housing terminates at a substantially continuous edge. A sterile cover may be attached to the substantially continuous edge of the housing for covering the housing and the tracking markers 1304, similar to patient reference device 600.

Still referring to FIG. 13, the device 1300 further comprises a strap connected to the rigid member 1302 for securing the device 1300 to a patient 202. In one example, the strap is attachable around a head of the patient 202. In another example, the device 1300 is securable to a patient 202 using a medical adhesive. The timeframe may be at least one frame of the 3-D scan and the field of view comprises the patient reference with the scanning range of the 3-D scanner 309 including the head of the patient 202.

Still referring to FIG. 13, the reference location comprises a fixed location such that the rigid member is attachable on a Mayfield head clamp, a bed, or a stretcher; and the connector mechanism is attachable to a back side of the rigid member 1302. In another example, the reference location comprises a location at which the rigid member is attached to a patient 202, rested on the skin of the patient 202, and the device 1300 may be wearable. The device 1300 further comprises a sterilizable and/or disposable material. While some examples are provided as to manners in which the device 1300 may be fabricated or mounted, the device 1300 comprises any of the characteristics described in connection with patient reference device 600, such as shown in FIGS. 6-9, for a particular application and are encompassed by the present disclosure.

Figure 14:
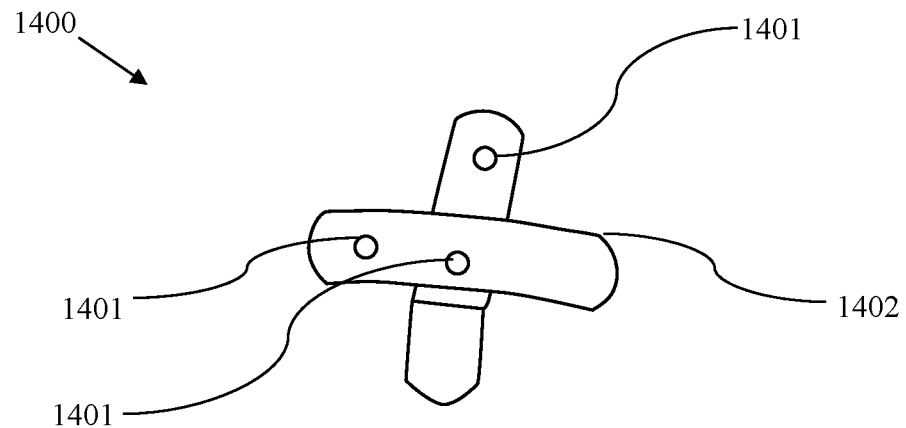
FIG. 14 is a diagram illustrating a perspective view of a trackable apparatus comprising at least one arrangement of at least one trackable feature configured for disposition in relation to at least one substrate, such as an adhesive substrate, e.g., a bandage, for use with a navigation system, such as a medical navigation system, in an environmental context, such as an operation room, in accordance with an embodiment of the present disclosure.

Referring to FIG. 14, this diagram illustrates, in a perspective view, a trackable apparatus 1400 comprising at least one arrangement of at least one trackable feature 1401 configured for disposition in relation to at least one substrate 1402, such as an adhesive substrate, e.g., a bandage, for use with a navigation system 200, such as a medical navigation system, in an environmental context, such as an operation room OR, in accordance with an embodiment of the present disclosure.

Still referring to FIG. 14, by example only, the at least one trackable feature 1401 comprises at least one of a tracking marker and a retroreflective material, e.g., integrated with the at least one substrate 1402 comprising an adhesive substrate, such as at least one of an adhesive tape and an adhesive bandage, wherein the adhesive substrate is readily disposable in relation to any object or subject in the operating room OR.

Still referring to FIG. 14, the at least one trackable feature 1401 further comprises a 3-D depth feature in relation to the adhesive substrate for further facilitating tracking and identifying objects and subjects, in accordance with another embodiment of the present disclosure. The at least one trackable feature 1401 further comprises a trackable deformable sticker that may be easily applied and tracked, in accordance with another embodiment of the present disclosure. By way of an adhesive substrate 1402, such as an adhesive tape, unique geometries or distinct arrangements of the at least one trackable feature are maintained for tracking by a tracking system 321, e.g., comprising an Optitrak® tracking system, of a navigation system 200, such as an optical tracking system of a medical navigation system. The at least one trackable feature 1401, comprising a retroreflective material, e.g., integrated with the at least one substrate 1402 comprising an adhesive substrate, is useful for applications, whereby surgical performance time is minimized, the chance of patient survival and recovery is optimized, the chance of medical malpractice is minimized, and the like.

Still referring to FIG. 14, by way of an adhesive substrate 1402, such as an adhesive tape, unique geometries or distinct arrangements of the at least one trackable feature are configurable for a number of applications, such use with a passive Stryker® mask, whereby back-calculation of features is facilitated, providing frameless tracking of a patient, use with a surgical cap, use with a surgical drape, and the like, whereby identifying subjects and objects by way of the unique geometries or the distinct arrangements is facilitated, the ability to combine optical imaging of a 3-D space is provided, a substitute for a retroreflective switch is provided, and accountability for deflection, e.g., significant deflection, and other changes, e.g., tolerance, for optimizing parameters, e.g., in an operating room OR, in terms of at least spatial relationships among the objects and subjects is provided.

Figure 15:
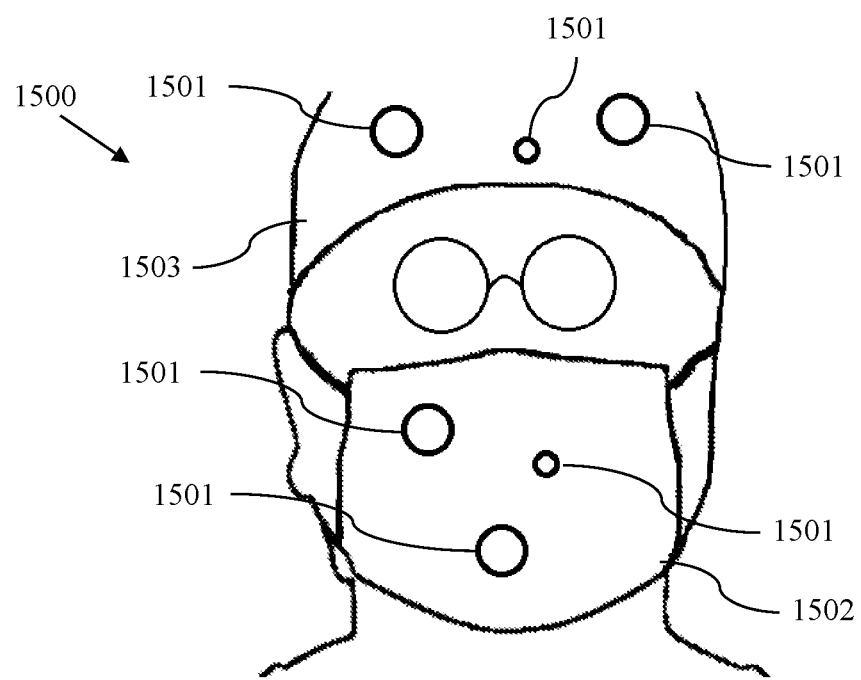
FIG. 15 is a diagram illustrating a perspective view of a trackable apparatus comprising at least one arrangement of at least one trackable feature configured for disposition in relation to at least one substrate, such as a surgical mask and a surgical cap, for use with a navigation system, such as a medical navigation system, in an environmental context, such as an operation room, in accordance with an embodiment of the present disclosure.

Referring to FIG. 15, this diagram illustrates, in a perspective view, a trackable apparatus 1500 comprising at least one arrangement of at least one trackable feature 1501 configured for disposition in relation to at least one substrate, such as a surgical mask 1502 and a surgical cap 1503, for use with a navigation system 200, such as a medical navigation system, in an environmental context, such as an operation room OR, in accordance with an embodiment of the present disclosure.

Still referring to FIG. 15, by example only, the at least one trackable feature 1501 comprises at least one of a tracking marker and a retroreflective material, e.g., integrated with, embedded in, or adhered to, the at least one substrate, such as the surgical mask 1502 and the surgical cap 1503, wherein each at least one arrangement of at least one trackable feature 1501 is distinct in relation to each subject, e.g., in the operating room OR, whereby medical personnel are uniquely identifiable, and whereby spatial relationship among at least one of an object and a subject, e.g., in the operating room OR, is determinable for at least preventing collision thereof, e.g., as between a robotic arm 305 and a surgeon 201.

Still referring to FIG. 15, in an embodiment of the present disclosure, the tracking markers comprise a geometry and a disposition that is compatible with at least one of guidelines and specifications of tithe optical tracking camera 307. Further, the trackable apparatus 1500 is configurable for positive-person-identification (PPID), whereby tracking identification and time performance of a surgeon 201 and other personnel, such as nurses, is provided.

Still referring to FIG. 15, the trackable apparatus 1500 comprising at least one arrangement of at least one trackable feature 1501 configured for disposition in relation to at least one substrate, such as a surgical mask 1502 and a surgical cap 1503, for use with a navigation system 200, such as a medical navigation system, in an environmental context, such as an operation room OR, provides a solution to the challenges faced in the rebated art by optically tracking the surgeon 201 and/or other medical personnel in relation to objects in a medical environment. The tracking system 321 of the navigation system 200 may comprise an infrared camera and use infrared techniques for tracking the trackable apparatus 1500 as the retroreflective feature is thereby visible and facilitates image guided surgery, in accordance with an embodiment of the present disclosure.

Still referring to FIG. 15, in such embodiments, the tracking markers having retro reflective features are embedded, coupled with, or integrally formed, in relation to the at least one substrate, such as the surgical mask 1502 and the surgical cap 1503, worn by the surgeon 201 in a manner such that at least one of the surgical mask 1502 and the surgical cap 1503 is in the optical tracking camera's line of sight. Using information regarding the position of the surgeon 201 along with the current position of the robotic arm 305, "gaze" information regarding the surgeon 201 is extractable and a "no fly zone" is determinable. The "no fly zone" generally denotes a volume within the line of sight of the optical tracking camera that the robotic arm 305 should not enter, whereby collision avoidance is provided, in accordance with an embodiment of the present disclosure.

Still referring to FIG. 15, when the robotic arm 305 is instructed to move, e.g., by the navigation system 200, a computed trajectory therefor is analyzed in relation to the "no fly zone" by the control and processing unit 300. If a spatial overlap between the computed robotic arm trajectory and the "no fly zone" is determined by the control and processing unit 300, the robotic arm trajectory is terminated and a new robotic arm trajectory is computed by the control and processing unit 300 of the navigation system 200, wherein a new instruction is provided to the drive or driver of the robotic arm 305. If the control and processing unit 300 is unable to determine a safe robotic arm trajectory in light of real-time events in the medical environment, e.g., the operating room OR, a warning is provided to the user, e.g., the surgeon 201 and/or other medical personnel, such as by at least one of an audible warning and a visual warning via the at least one display device 205.

Figure 16:
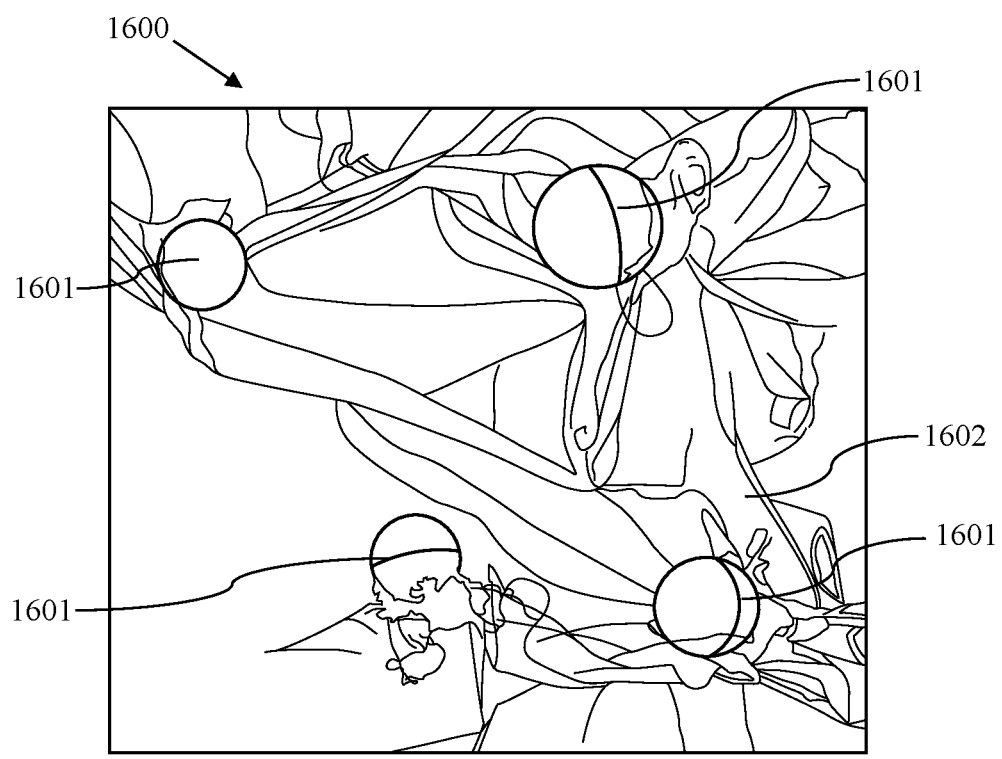
FIG. 16 is a diagram illustrating a perspective view of a trackable apparatus comprising at least one arrangement of at least one trackable feature configured for disposition in relation to at least one substrate, such as a surgical drape, for use with a navigation system, such as a medical navigation system, in an environmental context, such as an operation room, in accordance with an embodiment of the present disclosure.

Referring to FIG. 16, this diagram illustrates, in a perspective view, a trackable apparatus 1600 comprising at least one arrangement of at least one trackable feature 1601 configured for disposition in relation to at least one substrate, such as a surgical drape 1602, for use with a navigation system 200, such as a medical navigation system, in an environmental context, such as an operation room OR, in accordance with an embodiment of the present disclosure.

Still referring to FIG. 16, by example only, the at least one trackable feature 1601 comprises at least one of a tracking marker and a retroreflective material, e.g., integrated with, embedded in, or adhered to, the at least one substrate, such as the surgical drape 1602, wherein each at least one arrangement of at least one trackable feature 1601 is distinct in relation to each object, e.g., in the operating room OR, whereby medical equipment is uniquely identifiable, and spatial relationship among at least one of an object and a subject is determinable for at least preventing collision thereof, e.g., as between equipment and personnel.

Figure 17A:
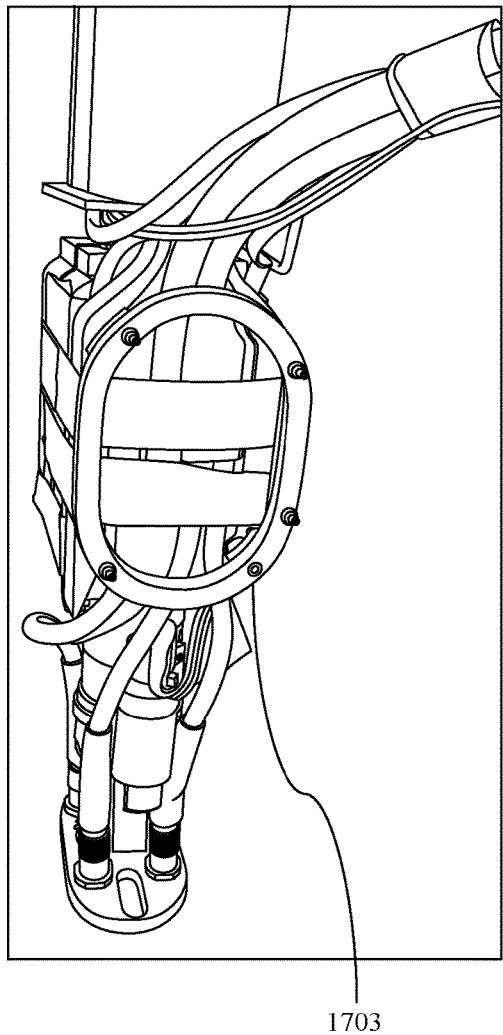
FIG. 17A is a diagram illustrating a perspective view of a piece of medical equipment, trackable by way of a drape having a trackable apparatus comprising at least one arrangement of at least one trackable feature, in accordance with an embodiment of the present disclosure.

Referring to FIG. 17A, this diagram illustrates, in a perspective view, a piece of medical equipment 1703, e.g., surgical equipment, trackable by way of a drape 1702 having a trackable apparatus 1700 comprising at least one arrangement of at least one trackable feature 1701 configured for disposition in relation to for use with a navigation system 200, such as a medical navigation system, in an environmental context, such as an operation room OR, in accordance with an embodiment of the present disclosure. The at least one trackable feature comprises at least one of a trackable marker and a retroreflective feature.

Figure 17B:
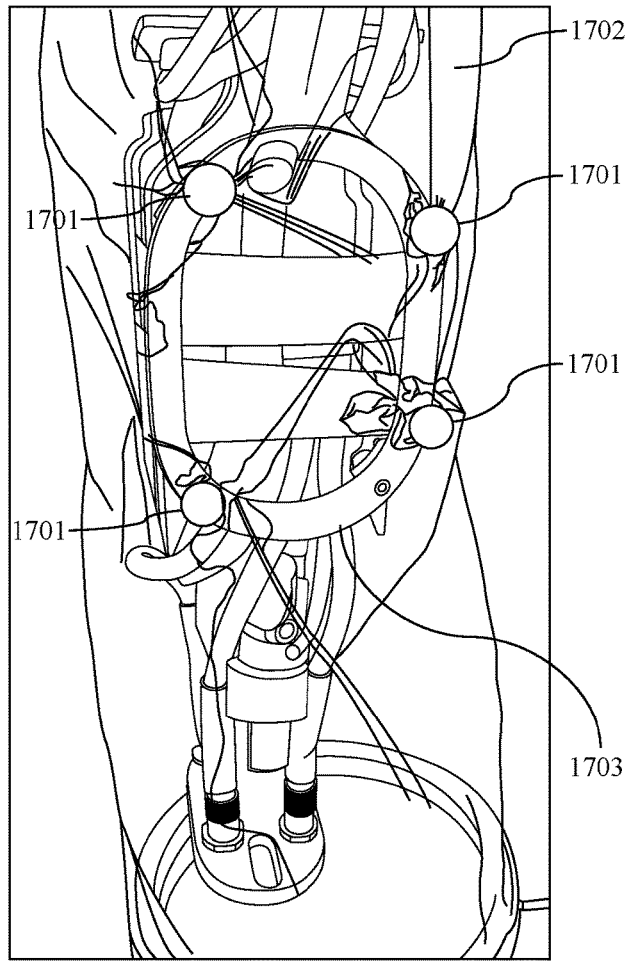
FIG. 17B is a diagram illustrating a perspective view of a piece of medical equipment, as shown in FIG. 17A, trackable by way of a drape, being disposed thereon, having a trackable apparatus comprising at least one arrangement of at least one trackable feature, in accordance with an embodiment of the present disclosure.

Referring to FIG. 17B, this diagram illustrates, in a perspective view, a piece of medical equipment 1703, e.g., surgical equipment, trackable by way of a drape 1702, being disposed thereon, having a trackable apparatus 1700 comprising at least one arrangement of at least one trackable feature 1701 configured for disposition in relation to for use with a navigation system 200, such as a medical navigation system, in an environmental context, such as an operation room OR, in accordance with an embodiment of the present disclosure. By example only, integrating the trackable apparatus 1700, comprising at least one of the at least one tracking marker and at least one retroreflective feature, into the drape 1702 minimizes the probability of damage to the drape 1702, otherwise compromising the sterile field as experienced in the related art. Also, integrating the trackable apparatus 1700, comprising at least one of the at least one tracking marker and at least one retroreflective feature, into the drape 1702 eliminates any error arising from related art attachment techniques, have some free-play, otherwise resulting in an error in the expected position and orientation of the piece of medical equipment 1703.

Still referring to FIG. 17B, the drape 1702 addresses a variety of challenges experienced in the related art. For instance, related art drapes generally comprise a clear rigid plastic material. Such related art drapes perform well if the related art drapes are disposed in an orientation that is perpendicular to the imaging direction of a camera, but the related art drapes do not perform well if the related art drapes are disposed in an orientation that is almost, but not quite, perpendicular (off-angle) due to a plurality of reflections. If the related art drapes are disposed in an orientation that is significantly far from perpendicular (highly off-angle), significant errors occur. As the related art tracking markers are recessed from the related art drape, the related art drape must remain in a plane perpendicular to the line of sight of the camera (which is impossible). Thus, related art drapes tend to behave as a lens, thereby distorting any distance calculation by any related art systems, and thereby limiting the degree to which the related art drape can be movable in relation to the camera without losing view of the related art tracking markers, and thereby having a refraction gradient which introduces larger errors. By at least integrating the trackable apparatus 1700, comprising at least one trackable feature, such as at least one of a trackable marker and a retroreflective feature, into the drape 1702 in the present disclosure, the trackable markers are adapted to move with the drape 1702 during a medical procedure, thereby maintaining trackability of the piece of equipment 1703 even during movement of the drape 1702.

Still referring to FIG. 17B, related art challenges include two problems: the camera's inability to view the moving related art tracking marker and the limited resolution of related art encoders and discrepancies in the related art model. As a non-sterile location may be far from the sterile field, the range limitations of a related art tracking camera and occlusion from equipment and staff render viewing the related art tracking marker impractical. Also, the error in the related art encoders and discrepancies in the distance between joints result in a stacking error that can be very large when the position and orientation of the desired location is resolved. By at least integrating the trackable apparatus 1700, comprising at least one trackable feature, such as at least one of a trackable marker and a retroreflective feature, into the drape 1702 in the present disclosure, the tracking marker is proximate the location to be tracked, thereby minimizing a potential for errors otherwise experienced in the related art.

Still referring to FIG. 17B, by at least integrating the trackable apparatus 1700, comprising at least one trackable feature, such as at least one of a trackable marker and a retroreflective feature, into the drape 1702 in the present disclosure, the tracking markers, such as tracking spheres need not be attached to the drape, thereby reducing preparation time by medical staff for at least that a use only needs to attach the drape itself. The tracking markers of the present disclosure are also configured to hold the drape in place.

Figure 18:
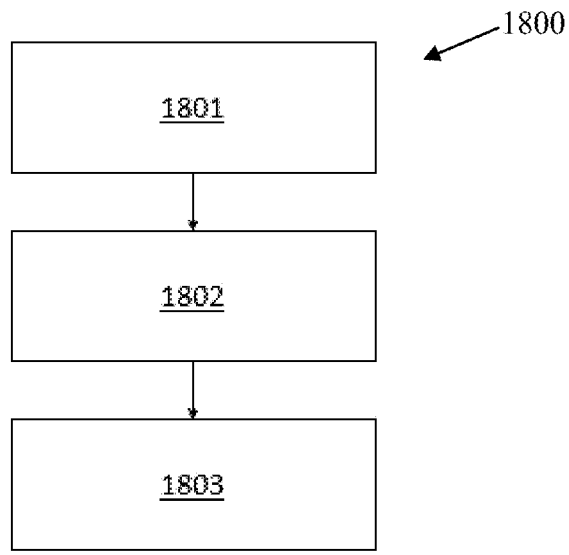
FIG. 18 is a flow chart illustrating a method of fabricating a trackable apparatus comprising at least one arrangement of at least one trackable feature configured for disposition in relation to at least one substrate, for use with a navigation system, in accordance with an embodiment of the present disclosure.

Referring to FIG. 18, this flow chart illustrates a method 1800 of fabricating a trackable apparatus, such as shown in FIGS. 14-16 and 17B, comprising at least one arrangement of at least one trackable feature configured for disposition in relation to at least one substrate, for use with a navigation system 200, in accordance with an embodiment of the present disclosure. The method 1800 comprises: configuring at least one arrangement of at least one trackable feature for disposition in relation to at least one substrate, as indicated by block 1801; configuring at least one arrangement comprising configuring each arrangement of the at least one arrangement in a distinct pattern of trackable features to facilitate determining at least one of: an identity of at least one object and at least one subject, a disposition of at least one object and at least one subject, a disposition between at least one object and at least one subject, and a disposition among at least one object and at least one subject, as indicated by block 1802; and configuring at least one arrangement comprising configuring each arrangement of the at least one arrangement to optimize tracking by a multi-modal tracking system, as indicated by block 1803, whereby at least one spatial relationship among the at least one object and the at least one subject is optimizable.

Still referring to FIG. 18, in the method 1800, the at least one trackable feature comprises at least one retroreflective feature. The at least one retroreflective feature is flexible and comprises a retroreflective tape. The at least one trackable feature further comprises at least one tracking marker. The multi-modal tracking system comprises a plurality of tracking devices. The plurality of tracking devices comprises at least two of at least one optical camera, at least one radio-frequency tracking device, at least one electromagnetic tracking device, and at least one inertial momentum unit (IMU) sensor.

Still referring to FIG. 18, each distinct pattern of trackable features optimizes detection by the multi-modal tracking system for warning of a potential spatial conflict among the at least one object and the at least one subject. Each distinct pattern of trackable features optimizes detection by the multi-modal tracking system by way of optimizing occlusion detection. The occlusion detection comprises detection of a distinct pattern trackable features that are identified with a surgical mask in relation to detection of a distinct pattern trackable features that are identified with a robotic arm, and whereby visibility is optimizable.

Still referring to FIG. 18, the at least one arrangement is configured for use in at least one of an operating room environment and a clinical environment. The at least one arrangement is configured for disposition in relation to the substrate in at least one manner of: attached in relation to the substrate, embedded in relation to the substrate, integrally formed in relation to the substrate, and proximately disposed in relation the substrate. The at least one substrate comprises at least one of a surgical tool, a surgical instrument, a surgical mask, a surgical cap, a surgical drape, a surgical scrub, and a therapeutic device.

Figure 19:
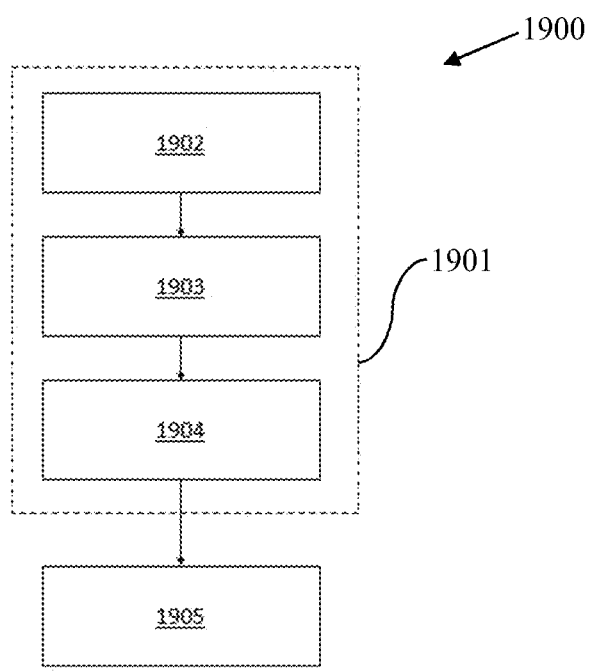
FIG. 19 is a flow chart illustrating a method of optimizing at least one spatial relationship among at least one object and at least one subject by way of a trackable apparatus, in accordance with an embodiment of the present disclosure.

Referring to FIG. 19, this flow chart illustrates a method 1900 of optimizing at least one spatial relationship among at least one object and at least one subject by way of a trackable apparatus, such as shown in FIGS. 14-16 and 17B, in accordance with an embodiment of the present disclosure. The method 1900 comprises: providing the trackable apparatus, as indicted by block 1901, providing the trackable apparatus comprising: configuring at least one arrangement of at least one trackable feature for disposition in relation to at least one substrate, as indicated by block 1902; configuring at least one arrangement comprising configuring each arrangement of the at least one arrangement in a distinct pattern of trackable features to facilitate determining at least one of: an identity of at least one object and at least one subject, a disposition of at least one object and at least one subject, a disposition between at least one object and at least one subject, and a disposition among at least one object and at least one subject, as indicated by block 1903; and configuring at least one arrangement comprising configuring each arrangement of the at least one arrangement to optimize tracking by a multi-modal tracking system, as indicated by block 1904; and disposing the at least one arrangement of the at least one trackable feature in relation to the at least one substrate, as indicated by block 1905, whereby at least one spatial relationship among the at least one object and the at least one subject is optimizable. The method 1900 further comprises tracking the at least one arrangement by way of the multi-modal tracking system, thereby optimizing the at least one spatial relationship among the at least one object and the at least one subject.

While the present disclosure describes various embodiments for illustrative purposes, such description is not intended to be limited to such embodiments. On the contrary, the applicant's teachings described and illustrated herein encompass various alternatives, modifications, and equivalents, without departing from the embodiments, the general scope of which is defined in the appended claims. Except to the extent necessary or inherent in the processes themselves, no particular order to steps or stages of methods or processes described in this disclosure is intended or implied. In many cases the order of process steps may be varied without changing the purpose, effect, or import of the methods described.

Information as herein shown and described in detail is fully capable of attaining the above-described object of the present disclosure, the presently preferred embodiment of the present disclosure, and is, thus, representative of the subject matter which is broadly contemplated by the present disclosure. The scope of the present disclosure fully encompasses other embodiments which may become obvious to those skilled in the art, and is to be limited, accordingly, by nothing other than the appended claims, wherein any reference to an element being made in the singular is not intended to mean "one and only one" unless explicitly so stated, but rather "one or more." All structural and functional equivalents to the elements of the above-described preferred embodiment and additional embodiments as regarded by those of ordinary skill in the art are hereby expressly incorporated by reference and are intended to be encompassed by the present claims.

Moreover, no requirement exists for a system or method to address each and every problem sought to be resolved by the present disclosure, for such to be encompassed by the present claims. Furthermore, no element, component, or method step in the present disclosure is intended to be dedicated to the public regardless of whether the element, component, or method step is explicitly recited in the claims. However, that various changes and modifications in form, material, work-piece, and fabrication material detail may be made, without departing from the spirit and scope of the present disclosure, as set forth in the appended claims, as may be apparent to those of ordinary skill in the art, are also encompassed by the present disclosure.

INDUSTRIAL APPLICABILITY

The subject matter of the present disclosure industrially applies to feedback and control systems for tracking items relating to medical procedures. More particularly, the subject matter of the present disclosure industrially applies to feedback and control systems for tracking items relating to surgical procedures. Even more particularly, the subject matter of the present disclosure industrially applies to the feedback and control systems for tracking items relating to image guided surgical procedures.

What is claimed:

1. A trackable apparatus, comprising:
   at least one arrangement of trackable features configured for disposition in relation to at least one corresponding substrate, the at least one arrangement configured to integrally form with the at least one corresponding substrate, each trackable feature of the at least one arrangement of trackable features comprising at least one retroreflective feature, the at least one corresponding substrate configured to couple with at least one of: at least one object and at least one subject, the at least one object comprising a robotic arm and a patient reference device comprising a housing having a matte finish, a cover, and seal disposed between the cover and the housing, the matte finish minimizing unwanted reflection to facilitate tracking by a tracking camera, the matte finish comprising a metal having a blasted finish and a hard anodization to decrease reflectivity of the housing,
   each arrangement of the at least one arrangement of trackable features forming a pattern distinct from another arrangement of the at least one arrangement of trackable features, each arrangement of the at least one arrangement of trackable features configured to facilitate determining at least one parameter of: an identity of the-at least one object and the at least one subject, a disposition of the at least one object and the at least one subject, a disposition between the at least one object and the at least one subject, and a disposition among the at least one object, comprising a plurality of objects, and the at least one subject, comprising a plurality of subjects, and each arrangement of the at least one arrangement of trackable features configured to facilitate multi-modally tracking the at least one object and the at least one subject by a multi-modal navigation tracking system,
   the multi-modal navigation tracking system comprising a plurality of tracking devices, and the plurality of tracking devices comprising an optical camera, an inertial momentum unit sensor, and at least one of a radio-frequency tracking device and an electromagnetic tracking device, the electromagnetic tracking device comprising a magnetometer,
   the multi-modal navigation tracking system coupled with a control and processing unit, the control and processing unit configured to: in real-time, in relation to events, corresponding to the at least one subject and the at least one object, in a medical environment,
      compute a trajectory of the robotic arm in relation to a no-fly zone,
      analyze a movement by the robotic arm along the computed trajectory of the robotic arm in relation to the no-fly zone for an overlap between the analyzed movement of the robotic arm along a portion of the computed trajectory in relation to the no-fly zone with the no-fly zone,
         determine a presence or absence of the overlap between the analyzed movement of the robotic arm along the portion of the computed trajectory in relation to the no-fly zone and the no-fly zone,
      wherein the presence of the overlap between the analyzed movement of the robotic arm along the portion of the computed trajectory in relation to the no-fly zone and the no-fly zone has been determined, then terminate the movement of the robotic arm along the portion of the computed trajectory of the robotic arm in relation to the no-fly zone; and
      determine if a safe trajectory of the robotic arm in relation to the no-fly zone can be computed, wherein the safe trajectory of the robotic arm in relation to the no-fly zone is computable then compute the safe trajectory of the robotic arm in relation to the no-fly zone and provide a new instruction, corresponding to the safe trajectory of the robotic arm in relation to the no-fly zone, to a driver of the robotic arm or wherein the safe trajectory of the robotic arm in relation to the no-fly zone is unable to be determined, terminate movement of the robotic arm in the computed trajectory of the robotic arm in relation to the no-fly zone; and provide a warning, the warning comprising at least one of an audible warning and a visual warning, and
      detect an acceleration of the patient reference device, determine if the detected acceleration is greater than a given threshold then force reregistration of the patient reference device,
      wherein the cover comprises a lens, and wherein the lens is configured to one of: transmit infrared light to the at least one arrangement of trackable features and to transmit reflected infrared light from the at least one arrangement of trackable features without diffraction, transmit infrared light while blocking light in at least one portion of a frequency spectrum on each side of an infrared pass band, and transmit only visible light if the at least one arrangement of trackable features comprises at least one graphical pattern,
      whereby multi-modal tracking of the at least one arrangement of trackable features in relation to the patient reference device is facilitated by the matte finish, and
      whereby collision of the at least one object with the at least one subject is avoided; and
   tracking the at least one arrangement by way of the tracking system, thereby optimizing the at least one spatial relationship among the at least one object and the at least one subject.

2. The apparatus of claim 1,
   wherein the at least one retroreflective feature is flexible, and
   wherein the at least one retroreflective feature further comprises at least one of a retroreflective tape and a retroreflective sphere.

3. The apparatus of claim 1,
   wherein at least one trackable feature of the at least one arrangement of trackable features further comprises at least one tracking marker, whereby the trackable apparatus is configurable for positive-person-identification,
   wherein the inertial momentum unit sensor further comprises at least one of an accelerometer, a gyroscope, a force sensor, a strain gauge, and any other suitable sensor, and
   wherein tracking identification and time performance of personnel comprising at least one of a surgeon, a nurse, and other personnel is provided.

4. The apparatus of claim 1, wherein each pattern of each arrangement of trackable features facilitates detection by the multi-modal navigation tracking system for warning of a potential collision of the at least one object with the at least one subject.

5. The apparatus of claim 1, wherein each pattern of each arrangement of trackable features facilitates detection by the multi-modal navigation tracking system by facilitating occlusion detection of the at least one object in relation to the at least one subject.

6. The apparatus of claim 5, wherein the occlusion detection comprises detection of a pattern that is identified as distinctive to a surgical mask in relation to detection of a pattern that is identified as distinctive to a robotic arm, and whereby visibility is facilitated.

7. The apparatus of claim 1, wherein the at least one arrangement is configured for use in a clinical environment.

8. The apparatus of claim 1, wherein the at least one corresponding substrate comprises at least one of: an adhesive substrate, a surgical tool, a surgical instrument, a surgical mask, a surgical drape, a surgical scrub, and a therapeutic device.

9. A method of optimizing at least one spatial relationship among at least one object and at least one subject by way of a trackable apparatus, comprising:

providing at least one arrangement of trackable features configured for disposition in relation to at least one corresponding substrate, providing the at least one arrangement comprising integrally forming the at least one arrangement with the at least one corresponding substrate, providing the at least one arrangement comprising providing each trackable feature of the at least one arrangement of trackable features as at least one retroreflective feature, providing the at least one arrangement comprising configuring the at least one corresponding substrate to couple with at least one of: at least one object and at least one subject, the at least one object comprising a robotic arm and a patient reference device comprising a housing having a matte finish, a cover, and seal disposed between the cover and the housing, the matte finish minimizing unwanted reflection to facilitate tracking by a tracking camera, the matte finish comprising a metal having a blasted finish and a hard anodization to decrease reflectivity of the housing, providing the at least one arrangement comprising forming each arrangement of the at least one arrangement of trackable features in a pattern distinct from another arrangement of the at least one arrangement of trackable features, each arrangement of the at least one arrangement of trackable features configured to facilitate determining at least one parameter of: an identity of the-at least one object and the at least one subject, a disposition of the at least one object and the at least one subject, a disposition between the at least one object and the at least one subject, and a disposition among the at least one object, comprising a plurality of objects, and the at least one subject, comprising a plurality of subjects, and each arrangement of the at least one arrangement of trackable features configured to facilitate multi-modally tracking the at least one object and the at least one subject by a multi-modal navigation tracking system, the multi-modal navigation tracking system comprising a plurality of tracking devices, and the plurality of tracking devices comprising an optical camera, an inertial momentum unit sensor, and at least one of a radio-frequency tracking device and an electromagnetic tracking device, the electromagnetic tracking device comprising a magnetometer, the multi-modal navigation tracking system coupled with a control and processing unit, the control and processing unit configured to: in real-time, in relation to events, corresponding to the at least one subject and the at least one object, in a medical environment, compute a trajectory of the robotic arm in relation to a no-fly zone, analyze a movement by the robotic arm along the computed trajectory of the robotic arm in relation to the no-fly zone for an overlap between the analyzed movement of the robotic arm along a portion of the computed trajectory in relation to the no-fly zone with the no-fly zone, determine a presence or absence of the overlap between the analyzed movement of the robotic arm along the portion of the computed trajectory in relation to the no-fly zone and the no-fly zone, wherein the presence of the overlap between the analyzed movement of the robotic arm along the portion of the computed trajectory in relation to the no-fly zone and the no-fly zone has been determined, then terminate the movement of the robotic arm along the portion of the computed trajectory of the robotic arm in relation to the no-fly zone; and determine if a safe trajectory of the robotic arm in relation to the no-fly zone can be computed, wherein the safe trajectory of the robotic arm in relation to the no-fly zone is computable then compute the safe trajectory of the robotic arm in relation to the no-fly zone and provide a new instruction, corresponding to the safe trajectory of the robotic arm in relation to the no-fly zone, to a driver of the robotic arm or wherein the safe trajectory of the robotic arm in relation to the no-fly zone is unable to be determined, terminate movement of the robotic arm in the computed trajectory of the robotic arm in relation to the no-fly zone; and provide a warning, the warning comprising at least one of an audible warning and a visual warning, and detect an acceleration of the patient reference device, determine if the detected acceleration is greater than a given threshold then force reregistration of the patient reference device, wherein the cover comprises a lens, and wherein the lens is configured to one of: transmit infrared light to the at least one arrangement of trackable features and to transmit reflected infrared light from the at least one arrangement of trackable features without diffraction, transmit infrared light while blocking light in at least one portion of a frequency spectrum on each side of an infrared pass band, and transmit only visible light if the at least one arrangement of trackable features comprises at least one graphical pattern, whereby multi-modal tracking of the at least one arrangement of trackable features in relation to the patient reference device is facilitated by the matte finish, and whereby collision of the at least one object with the at least one subject is avoided; and tracking the at least one arrangement by way of the tracking system, thereby optimizing the at least one spatial relationship among the at least one object and the at least one subject.

10. The method of claim 9,
wherein the at least one retroreflective feature is flexible, and
wherein the at least one retroreflective feature further comprises at least one of a retroreflective tape and a retroreflective sphere.

11. The method of claim 9,
wherein providing the at least one arrangement of trackable features further comprises providing at least one trackable feature of the at least one arrangement of trackable features as at least one tracking marker, whereby the trackable apparatus is configurable for positive-person-identification,
wherein the inertial momentum unit sensor further comprises at least one of an accelerometer, a gyroscope, a force sensor, a strain gauge, and any other suitable sensor, and
wherein tracking identification and time performance of personnel comprising at least one of a surgeon, a nurse, and other personnel is provided.

12. The method of claim 9, wherein at least one of:
each pattern of each arrangement of trackable features facilitates detection by the multi-modal navigation tracking system for warning of a potential collision of the at least one object with the at least one subject,
each pattern of each arrangement of trackable features facilitates detection by the multi-modal navigation tracking system by facilitating occlusion detection of the at least one object in relation to the at least one subject,
the occlusion detection comprises detection of a pattern that is identified as distinctive to a surgical mask in relation to detection of a pattern that is identified as distinctive to a robotic arm, and whereby visibility is facilitated,
the at least one arrangement is configured for use in a clinical environment, and
the at least one corresponding substrate comprises at least one of: an adhesive substrate, a surgical tool, a surgical instrument, a surgical mask, a surgical drape, a surgical scrub, and a therapeutic device.

* * * * *